US012408857B1

(12) United States Patent
Hatamian et al.

(10) Patent No.: US 12,408,857 B1
(45) Date of Patent: Sep. 9, 2025

(54) CARDIAC MONITORING SYSTEM WITH AUTOMATIC DETECTION OF WIRELESS ELECTRODE POSITIONING

(71) Applicants: Mehdi Hatamian, Mission Viejo, CA (US); Charbel Maksoud, Loma Linda, MO (US)

(72) Inventors: Mehdi Hatamian, Mission Viejo, CA (US); Charbel Maksoud, Loma Linda, MO (US)

( * ) Notice: Subject to any disclaimer, the term of this patent is extended or adjusted under 35 U.S.C. 154(b) by 0 days.

(21) Appl. No.: 18/981,417

(22) Filed: Dec. 13, 2024

Related U.S. Application Data

(60) Provisional application No. 63/613,021, filed on Dec. 20, 2023.

(51) Int. Cl.
*A61B 5/308* (2021.01)
*A61B 5/271* (2021.01)
*A61B 5/28* (2021.01)
*A61B 5/304* (2021.01)
*A61B 5/339* (2021.01)

(52) U.S. Cl.
CPC ............. *A61B 5/339* (2021.01); *A61B 5/271* (2021.01); *A61B 5/28* (2021.01); *A61B 5/304* (2021.01); *A61B 5/308* (2021.01)

(58) Field of Classification Search
None
See application file for complete search history.

(56) References Cited

U.S. PATENT DOCUMENTS

| | | | |
|---|---|---|---|
| 4,121,573 A | 10/1978 | Crovella et al. | |
| 5,307,818 A | 5/1994 | Segalowitz | |
| 6,496,705 B1 | 12/2002 | Ng et al. | |
| 6,577,893 B1 | 6/2003 | Besson et al. | |
| 6,611,705 B2 | 8/2003 | Hopman et al. | |
| 9,861,290 B1 | 1/2018 | Grek et al. | |
| 10,244,986 B2 | 4/2019 | Adams | |
| 11,116,401 B2 | 9/2021 | Bedingham et al. | |
| 2002/0045836 A1* | 4/2002 | Alkawwas | A61B 5/318 600/509 |
| 2003/0199777 A1 | 10/2003 | Hopman et al. | |

(Continued)

FOREIGN PATENT DOCUMENTS

EP 2262419 6/2019

*Primary Examiner* — Kennedy Schaetzle
(74) *Attorney, Agent, or Firm* — Makoui Law, PC; Ali Makoui

(57) ABSTRACT

A cardiac monitoring system that automatically determines whether one or more electrodes are placed at wrong positions on a person's body includes an ECG monitor. The electrodes are connected to the ECG monitor wirelessly or by wire. Each electrode includes a position code that corresponds to a body location where the electrode is to be placed. The signals that are transmitted from each electrode include the position code assigned to the electrode. The profile of the signals received from the electrodes are compared with expected profile of the signals from the electrodes that are placed at each specific position on the body. The position code in the transmitted data of any electrode that is determined to be placed at a wrong position is automatically replaced with the position code corresponding to the electrodes' actual position. The leads are then determined based on the electrode signals and the electrodes' position codes.

9 Claims, 22 Drawing Sheets

(56) References Cited

U.S. PATENT DOCUMENTS

| | | |
|---|---|---|
| 2004/0068195 A1 | 4/2004 | Massicotte et al. |
| 2004/0073127 A1 | 4/2004 | Istvan et al. |
| 2009/0088608 A1* | 4/2009 | Mumford .............. A61B 5/4041 |
| | | 600/300 |
| 2009/0099469 A1* | 4/2009 | Flores ...................... A61B 5/25 |
| | | 600/523 |
| 2010/0234746 A1 | 9/2010 | Sebelius |
| 2020/0037877 A1 | 2/2020 | Ott et al. |
| 2020/0155002 A1* | 5/2020 | Nandi ........................ A61B 5/25 |
| 2023/0026212 A1* | 1/2023 | Brodnick ................ A61B 5/282 |
| 2024/0041378 A1* | 2/2024 | Tufvesson ................ A61B 5/70 |
| 2024/0225444 A1* | 7/2024 | Saleh ................... A61B 5/0006 |

\* cited by examiner

CARDIAC MONITORING SYSTEM WITH AUTOMATIC DETECTION OF WIRELESS ELECTRODE POSITIONING

CLAIM OF BENEFIT TO PRIOR APPLICATIONS

This application claims the benefit of U.S. Provisional Patent Application Ser. No. 63/613,021, filed on Dec. 20, 2023. The contents of U.S. Provisional Patent Application 63/613,021 are hereby incorporated by reference.

BACKGROUND

An electrocardiogram (ECG or EKG) is a recording of the heart's electrical activity using electrodes placed on the skin. Each electrode is a conductive pad attached to the skin to receive electrical currents. Each heartbeat (or cardiac cycle) creates small electrical signals as a result of depolarization and repolarization of the cardiac muscle. The electrodes placed on the skin detect small electrical changes that are created by the cardiac muscle. Deviations from a normal ECG pattern in a patient may indicate a cardiac abnormality.

An ECG lead signal is a representation of the electrical activity of the heart often presented graphically as a waveform displaying the amplitude of the lead's signal vs. time. Each lead represents the difference in electrical potential between an exploring (or positive) electrode and one or more references (or negative) electrodes. For example, in some leads, the reference is a combination of the potentials at two or three electrodes. In other leads, the reference is the potential at one reference electrode.

In a 12-lead ECG, ten electrodes are placed on the limbs and chest of a patient. The heart's electrical potential is then measured from twelve different leads (or angles). There are two types of leads in typical ECG waveforms: limb leads (I, II, III, aVR, aVL, and aVF) and chest or precordial leads (C1, C2, C3, C4, C5, and C6). The leads (aVR, aVL, and aVF) are also referred to as unipolar or augmented leads. The leads (I, II, and III) are also referred to as bipolar leads. Other ECG lead systems such as 1-lead ECGs that use two electrodes, 3-lead ECGs that use three electrodes, 5-lead ECGs that use five electrodes, and 6-lead ECGs that use 6 electrodes are also commonly used.

BRIEF DESCRIPTION OF THE DRAWINGS

The various embodiments of the present cardiac monitoring system now will be discussed in detail with an emphasis on highlighting the advantageous features. These embodiments depict the novel and non-obvious cardiac monitoring system shown in the accompanying drawings, which are for illustrative purposes only. These drawings include the following figures, in which like numerals indicate like parts.

DETAILED DESCRIPTION

Figure 1:
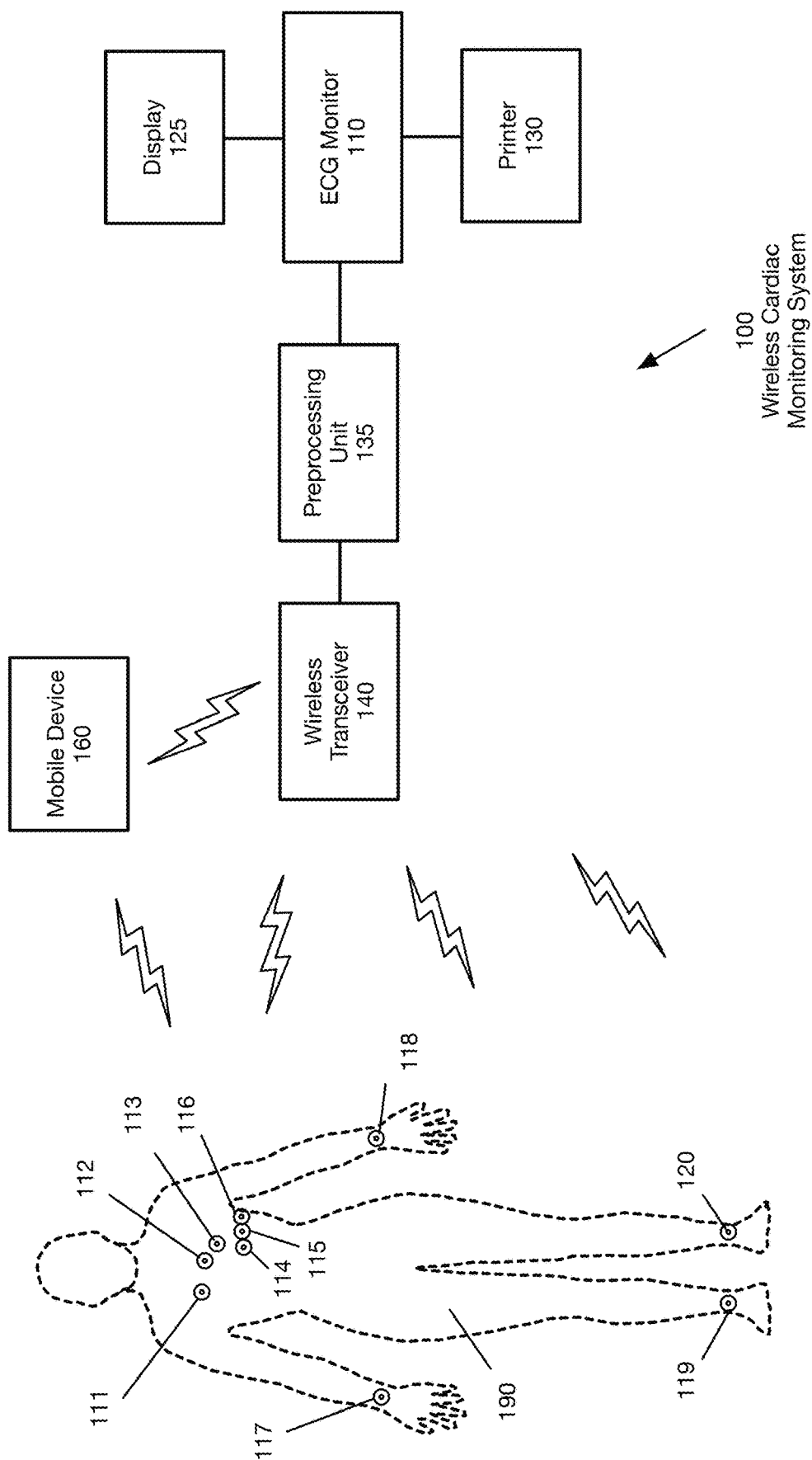
FIG. 1 is functional diagram of one example embodiment of a wireless cardiac monitoring system, according to various aspects of the present disclosure.

One aspect of the present embodiments includes the realization that each electrode of the existing cardiac monitoring systems has to be placed on a specific location on the body of a person. Each electrode may have a unique color to assist in proper positioning of the electrode on the body. In the wired cardiac monitoring systems, the signal from each electrode comes to the input ports of the cardiac monitoring system through a specific wire. The cardiac monitoring system, therefore, identifies the electrodes based on their corresponding wires.

If an electrode is placed at a wrong position on the body, a traditional cardiac monitoring system still determines the leads based on the expected (rather than the actual) position of the electrode, resulting in an incorrect ECG. In the existing cardiac monitoring systems, if an electrode is placed at a wrong position, the medical personnel in attendance have to find out that the electrode is placed at the wrong position by looking at the ECG recording. The medical personnel have to find any electrodes that is placed at a wrong position, physically remove the electrode, place it on the expected position, and repeat the ECG recording. Failure to physically place all electrodes at their expected positions invariably results in an incorrect ECG.

The present embodiments, as described in detail below, solve the above-mentioned problems by providing a cardiac monitoring system that automatically determines whether one or more electrodes are placed at wrong positions on a person's body. The cardiac monitoring system may include an ECG monitor, and the electrodes may be connected to ECG monitor wirelessly or by wire.

The embodiments where the electrodes are wireless may assign a position code to each wireless electrode. The position code of each electrode is a unique code that corresponds to the body location where the electrode is to be placed. The signals that are transmitted from each electrode include the position code assigned to the electrode. The position code in the transmitted data of any electrode that is determined to be placed at a wrong position is automatically replaced with the position code corresponding to the electrodes' actual position. The leads are then determined based on the electrode signals and the electrodes' position codes.

In the embodiments where the electrodes are wired, the wire from any electrode that is placed at a wrong position is routed by a connection box to an input of the ECG monitor that corresponds to the electrode's actual position.

Some embodiments perform experiments to identify and learn the expected profile of the signals (e.g., the shape and or the contours of the signals) received from the electrodes that are placed at each specific position on the body. The identified profiles are stored as the expected signal profiles of the electrodes placed at specific positions on the body. The identified signal profile of each electrode is associated with the unique position code that corresponds to the body position where the electrode is expected to be placed.

During operation, the electrode signals transmitted to the wireless cardiac monitoring system includes the unique position codes assigned to the electrodes. The electrode signal profiles are compared to the stored expected signal profile associated with the position code in the electrode signal. When the profile of an electrode signal does not match the corresponding expected profile, the stored expected profiles are searched to identify a stored profile that matches the electrode's signal profile. The position code of the stored profile that matches the electrode's signal is used to identify the actual position of the electrode. The position code in the electrode's signal is then replaced by the position code for the actual position of the electrode. The position codes of other electrodes that are located at wrong positions are similarly changed. The cardiac monitoring system then generates the ECG leads by using the updated electrode position codes.

In the embodiments where the electrodes are connected to the cardiac monitoring device by wires, the cardiac monitoring device may include several analog inputs. Each analog input may be programmed to receive a signal from an electrode located at a particular position on the body. Some of the present embodiments may include a connection box between the electrodes and the ECG monitor of the cardiac monitoring device.

The connection box may include several inputs. Each input may receive a wire from one of the electrodes. The connection box may include several outputs. Each output may be connected to an analog input of the ECG monitor of the cardiac monitoring device. In these embodiments, the electrode signal profiles are compared to the stored expected signal profile associated with the electrode wire connected to the electrode. When the profile of an electrode signal does not match the corresponding expected profile, the stored expected profiles are searched to identify a stored profile that matches the electrode's signal profile. After the actual position of an electrode that is wrongly positioned on the body is determined, the connection box may route the signal from the electrode to the analog input of the ECG monitoring that is programmed to receive the signal from the electrode that is located at the actual position.

In some embodiments with wireless or wired electrodes, the electrodes may have a visual indicator (e.g., color, tag, etc.) that identify the expected position of the electrode on the body. Some of these embodiments may require one or more color images to be taken from the electrodes that are placed on a person's body. The color image(s) of the electrodes placed on the body may be analyzed by a processor of the cardiac monitoring system to determine whether the electrodes are correctly placed on the body. Since each electrode with a visual identifier (e.g., a color code) has to be placed at a predetermined position on the body, any electrode that is incorrectly positioned may be identified when the actual position of a color-coded electrode does not match the expected position of the electrode.

In some embodiments that analyze the color image(s), a message may be generated to instruct the healthcare personnel in attendance to remove the electrodes that are placed at wrong positions and place them at correct positions (i.e., the positions that match the visual indicator and/or the position codes of the electrodes). The message may identify the visual indicator of the electrodes that are placed at wrong positions.

Other embodiments may automatically mitigate when the analysis of the color image(s) indicate that one or more electrodes are placed at wrong positions without requiring the electrodes to be physically moved. In some of these embodiments where the electrodes are wireless, the position code in the transmitted data of any electrode that is determined to be placed at a wrong position is automatically replaced with the position code corresponding to the electrodes' actual position. In some of these embodiments where the electrodes are wired, the wire from any electrode that is placed at a wrong position may be routed by a connection box to an input of the cardiac monitoring system that corresponds to the electrode's actual position.

The remaining detailed description describes the present embodiments with reference to the drawings. In the drawings, reference numbers label elements of the present embodiments. These reference numbers are reproduced below in connection with the discussion of the corresponding drawing features.

FIG. 1 is functional diagram of one example embodiment of a wireless cardiac monitoring system 100, according to various aspects of the present disclosure. With reference to FIG. 1, the wireless cardiac monitoring system 100 may include an ECG monitor 110, a preprocessing unit 135, a wireless transceiver 140, and several wireless electrodes 111-120. The wireless cardiac monitoring system 100 may include a display 125 and/or a printer 130.

The wireless electrodes 111-120 may be connected to the body of a person 190 that may be lying on a bed. The wireless electrodes 111-120 may receive electric signals from the person's 190 heart, may digitize the signals, and may wirelessly transmit the digitized signals to the wireless transceiver 140 of the wireless cardiac monitoring system 100 and/or to one or more mobile devices 160. Each wireless electrode 111-120 may include a position code that correspond to a specific position on the body of the person where the electrode is expected to be positioned. Each wireless electrode 111-120 may include its position code in the digitized data that the wireless electrode transmits to the wireless transceiver 140 and/or the mobile device(s) 160. It should be noted that the person 190 is not a part of the cardiac monitoring systems of the present embodiments and is shown to demonstrate how the electrodes may be attached to a person.

Different embodiments may use different types of wireless electrodes. The wireless electrodes, in some embodiments may be self-contained electrodes that may sense the electrical activity locally and wirelessly transmit the results to the preprocessing unit 135 via the circuitry integrated inside the electrodes for further processing.

In other embodiments, where it may be desired to directly sense the differential signal between two individual wireless electrodes, a physical connection via a short wire may be made between two or more electrodes. The sensed differential signal may be digitized and wirelessly transmitted to the preprocessing unit 135 via the circuitry integrated inside the electrodes for further processing. Examples of wireless electrodes that are connected together are described below with references to FIGS. 4D-4E.

In some embodiments, all wireless electrodes may be connected with a wire to one reference electrode. In this case the differential signal sensed between each wireless electrode and the reference electrode may be digitized and wirelessly transmitted to the preprocessing unit 135 via where the difference between any two electrodes (a lead or a channel as is commonly referred to) may be easily calculated. The wire connections in this arrangement may be permanently made between each electrode and the reference electrode or may be made via magnetic connections after placing the electrodes on the body of the subject as described above.

The preprocessing unit 135 may identify the position code in each received signal from the wireless electrodes 111-120 and may compare the profile of the received signals with the expected signal profiles corresponding to the position codes to determine whether the electrodes are placed at the corresponding expected positions on the body of the person 190. The preprocessing unit 135 may identify the actual position of any electrode that is placed on a wrong body position based on the profile of the signal received from the electrode. For an electrode that is placed at a wrong position, the preprocessing unit 135 may replace the position code that the electrode includes in the electrode's transmitted data with the position code that corresponds to the actual position of the electrode. The ECG monitor 110 may then use the data with the position codes that correspond to the actual positions of the electrodes to determine the leads without requiring the electrodes that are positioned at wrong places of the body to be physically moved.

The following are non-limiting examples of how the profiles of the received signals may be compared with the profiles of the expected signal. The profile of the received signals, in some embodiments, may be compared with the expected signal profiles as follows. As a first level comparison step, for a given lead waveform, the lead signal may be processed in time domain and the position in time of all the peaks and valleys (e.g., the maximum and minimum points) of the signal and their amplitudes may be found. The polarities, amplitudes, relative time positions, and the number of these peaks and valleys may be compared with the expected values from the reference signal for that particular lead and if the difference is larger than a pre-set value, an error signal may be generated As a further step in performing the comparison, the digitized waveforms of the leads may be compared against the expected waveform point by point and an error signal equal to the sum of the square of the differences between the amplitude of each point of the lead waveform and the corresponding point of the expected waveform may be calculated. If the value of this error signal is larger than a threshold, it may be determined that the profile of the received signal does not match the expected signal profile.

The ECG waveforms, in some embodiments, may include a sync pulse at the beginning of each lead waveform. For example, in the wireless cardiac monitoring system 100 shown in FIG. 1, the processor of the ECG monitor 110) may issue a sync command to all the electrodes to start recording at the same time. In a wired cardiac monitoring system, such as the wired cardiac monitoring system 300 shown in FIG.

3, the processor of the ECG monitor 110 may also generate a sync pulse at the beginning of each lead waveform. These sync pulses facilitate the line-up of the lead waveform with the corresponding expected waveform for the purpose of the difference calculation mentioned above. In the absence of the sync pulses, a cross correlation operation or a peak detection operation may first be performed between the lead waveform and the expected waveform to line up the two signals for the difference operation.

There is a vast amount of ECG waveform data available for each lead or channel for both healthy subjects and patients with heart conditions. Some embodiments may train an artificial intelligence (AI) algorithm with the available ECG waveform data to classify the combination of the lead waveforms into one of three main categories of (a) healthy, (b) heart disease, and (c) wrong electrode placement. The lead waveforms that fall into category "c" occur when neither of the categories "a" or "b" are detected. A further sub-classification of category "b" may also provide an indication of the possibility of the type of detected heart disease.

For a 12-lead ECG arrangement, if each one of the 12 lead waveforms is sampled at, for example, 1 KHz for 10 seconds with a 16-bit analog to digital converter (ADC), 10,000 sample points may be collected for each waveform. The input to the AI algorithm, in this example, may be a set of 12 vectors where each vector has a length of 10,000 elements (10,000 data points each 16 bits) for 120,000 total data point for an ECG from one subject.

In some embodiments, where the location of a reference electrode is verified to be correct, the waveform signal from each electrode compared to the reference electrode is compared with a set of expected pre-recorded signals to determine the electrodes that are positioned incorrectly and where the correct position should be. For example, in a 12-lead ECG the system may identify that a first electrode's signal corresponds to what is expected from a second electrode and the position code received from the first electrode may be replaced by the position code of the second electrode as described below with reference to FIG. 2.

In some embodiments, a data set of all the waveforms corresponding to all possible conditions for wrong electrode placement may be generated (e.g., by actual experiments or by simulation) and may be stored for comparison with a new ECG data set for detecting errors in electrode positions. While for large number of electrodes (e.g. 10 electrodes in a 12-lead ECG) this may be a time-consuming task, but it is done only once. As an example, for a 12-lead ECG with 10 electrodes the possible combinations may be 3,628,800 resulting in a data base of the size of approximately 871 GB of storage which is easily manageable. For a 6 electrode ECG example, the number of combinations is reduced to only 720 and the required storage to only about 172 MB.

In addition, a number of error conditions in electrode placement may be detected easily. As an example, if the waveform for a certain lead between two electrodes is the inverse of what is expected, then it points to an error where the position of the two electrodes are transposed.

Figure 2:
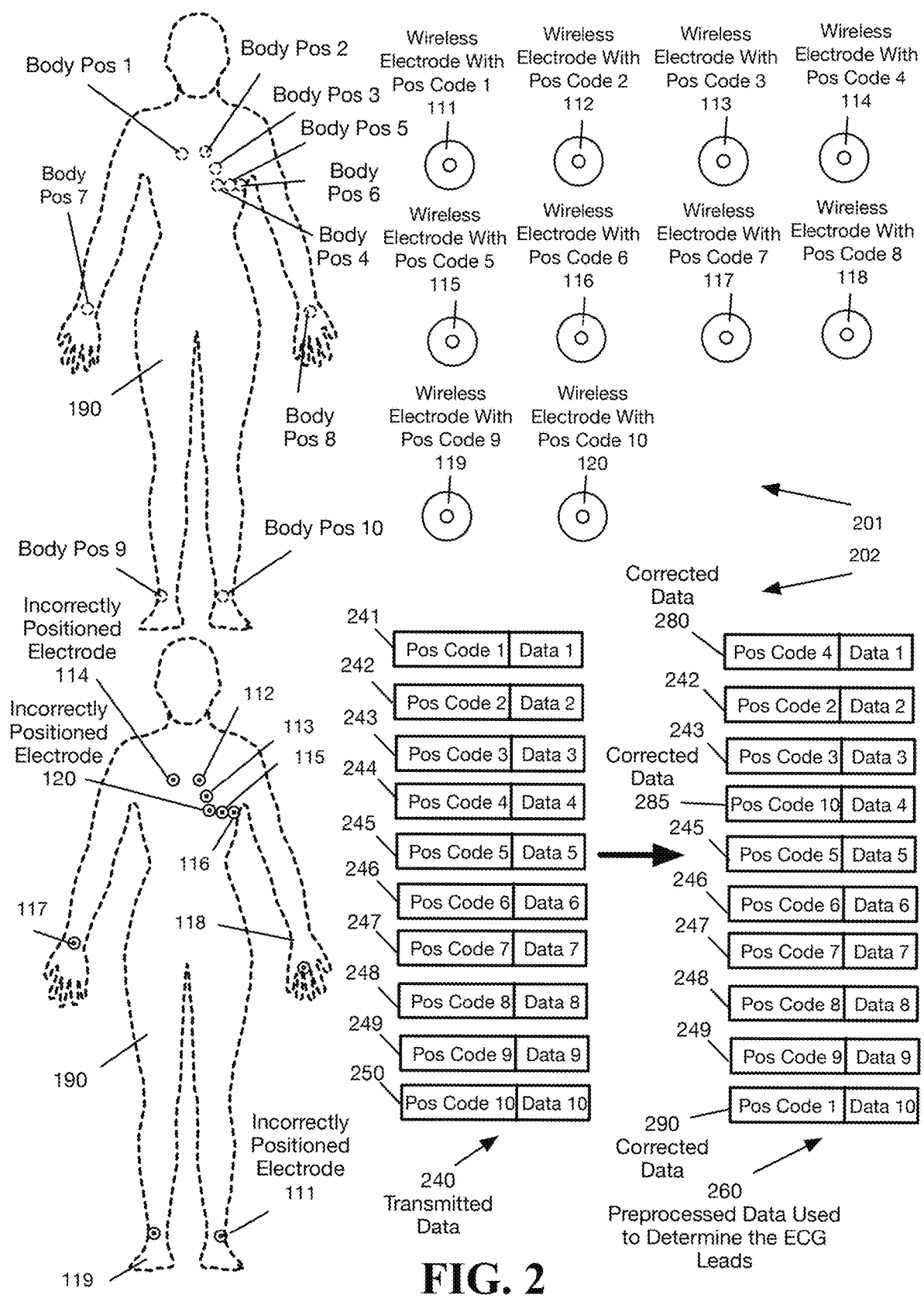
FIG. 2 is a functional diagram of one example embodiment of the wireless cardiac monitoring system of FIG. 1, illustrating the transmitted data of the electrodes modified to replace the position codes of the electrodes that are placed on the wrong locations on the body with position codes that correspond to the electrodes' actual positions, according to various aspects of the present disclosure.

FIG. 2 is a functional diagram of one example embodiment of the wireless cardiac monitoring system of FIG. 1, illustrating the transmitted data of the electrodes modified to replace the position codes of the electrodes that are placed at wrong locations on the body with position codes that correspond to the electrodes' actual positions, according to various aspects of the present disclosure. The example of FIG. 2 is described for a 12-lead ECG system that includes 10 electrodes. It should be noted that the same description applies to ECG system with different numbers of leads and electrodes.

FIG. 2, as shown, includes two stages 201-202. Stage 201 shows the 10 positions (Body Pos 1 to Body Pos 10) on the body of the person 190 were the 10 ECG electrodes 111-120 have to be placed for a 12-lead (10 electrode) ECG system.

As shown in stage 201, each wireless electrode 111-120 may have an assigned position code that corresponds to one of the 10 positions on the body of the person 290. Each wireless electrode 111 to 120 may include computer readable media to store the assigned position code. Each electrode may have a unique visual indicator (e.g., a color, a visual tag, etc.) to assist a healthcare personnel to place the electrode on a corresponding position Body POS 1 to Body POS 10 on the body of the person 190.

In stage 202, the electrodes 111-120 are placed on the body of the person 190. As shown, several electrodes 111, 114, and 120 are placed at wrong positions. For example, despite each electrode having a visual indicator that indicates where the operator has to place the electrode, the electrodes 111, 114, and 120 are placed at wrong positions due to the operator's error. For the electrodes 111, 114, and 120 that are placed at wrong positions, the position codes of the electrodes do not match the position code of the body locations where the electrodes are placed.

The transmitted data 241-250 of the electrodes 111-120 is shown by 240. The transmitted data of each electrode includes the electrode's assigned position. The preprocessing unit 135 (FIG. 1) may determine the actual position of the electrodes by comparing the electrodes' signal profiles with expected profiles of the electrode's signals (e.g., the stored expected profile corresponding to the position code transmitted by the electrode).

The preprocessed data used by the cardiac monitoring system to determine the ECG leads is shown by 260. As shown, the data 280, 285, and 290 respectively associated with the electrodes 111, 114, and 120 is corrected by the preprocessing unit 135 and the position codes transmitted by the electrodes that are placed at wrong positions are replaced with the position codes associated with the electrodes' actual positions.

Referring back to FIG. 1, the ECG monitor 110, in some embodiments, may be a legacy (or conventional) ECG monitor that may require analog inputs. In these embodiments, the preprocessing unit 135 may convert the digitized signals received from the wireless electrodes 111-120 into analog signals that are recognizable by the legacy ECG monitor, thereby avoiding the purchase of a new ECG monitor or training the staff to use a new ECG monitor. The legacy ECG monitors may include several input ports and may be configured to correctly process signals from the electrode patches only when each input port receives a signal from an electrode patch that is placed at a specific location on the body of the person.

In the embodiments that the ECG monitor 110 is a legacy ECG monitor, the preprocessing unit 135 may provide the converted analog signal of each electrode to the input port of the legacy ECG monitor that corresponds to the actual position of the electrode. In other embodiments, the ECG monitor 110 may be an ECG monitor that may be capable of receiving and processing electrode signals as digital data.

The ECG monitor 100 may include a processor and computer readable media. In the embodiments that the ECG monitor 110 is a legacy ECG monitor, the preprocessing unit 135 may also include a processor and computer readable media. In some of the embodiments that the ECG monitor is capable of receiving and processing electrode signals as digital data, the preprocessing unit 135 may be a software component of the ECG monitor and may use the processor and computer media of the ECG monitor 110. In other embodiments that the ECG monitor is capable of receiving and processing electrode signals as digital data, the preprocessing unit 135 and the ECG monitor 110 may include separate processors and separate computer readable media.

Figure 3:
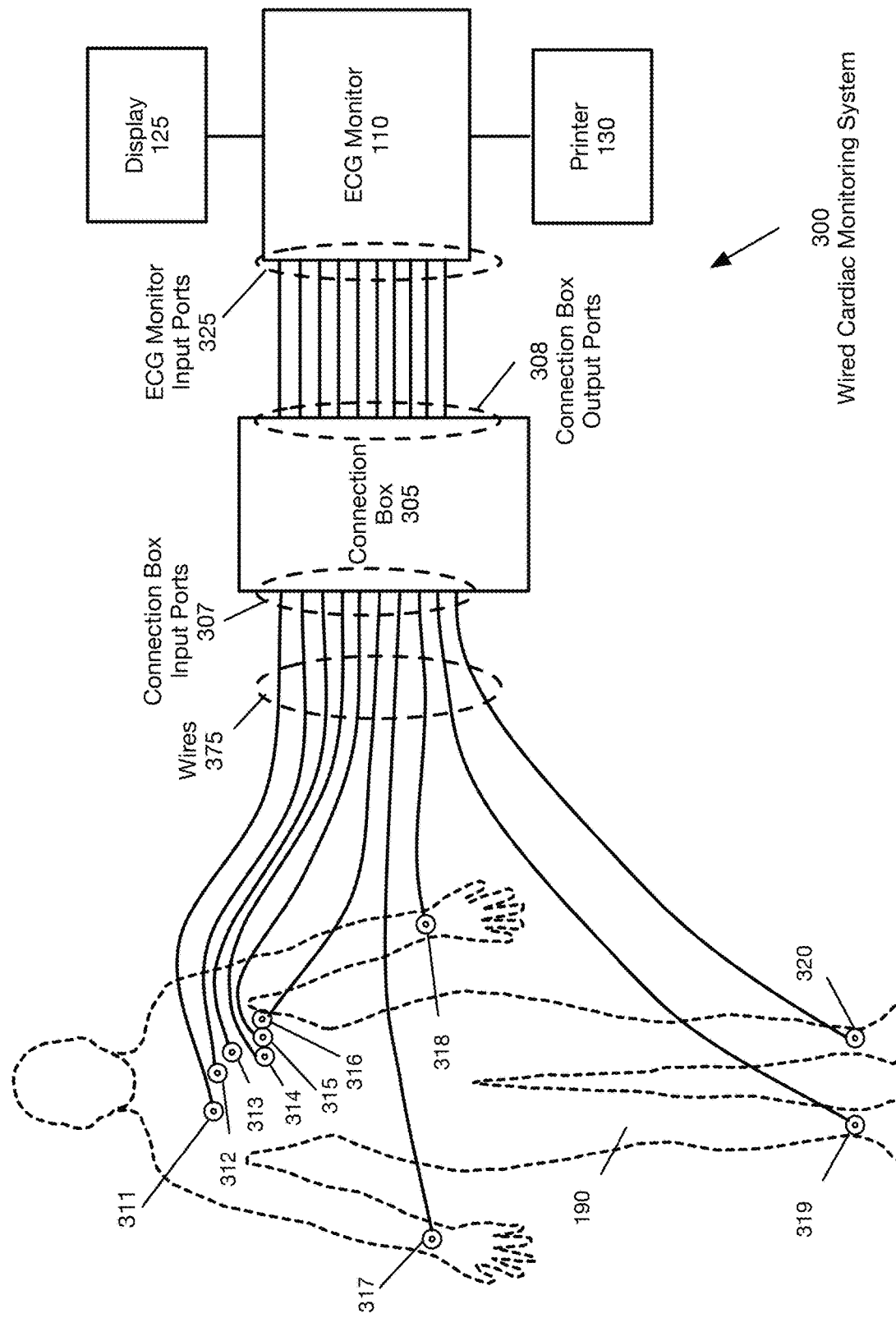
FIG. 3 is functional diagram of one example embodiment of a wired cardiac monitoring system, according to various aspects of the present disclosure.

FIG. 3 is functional diagram of one example embodiment of a wired cardiac monitoring system 300, according to various aspects of the present disclosure. With reference to FIG. 3, the cardiac monitoring system 300 may include an ECG monitor 110, a connection box 305, and several electrode patches 311-320. The cardiac monitoring system 300 may include a display 125 and/or a printer 130.

The electrode patches 311-320, in some embodiments, may be legacy (or conventional) electrode patches that are commonly used in the existing ECG systems. The electrode patches 311-320 may receive electric signals from the person's 190 heart and may transmit the signals, through the corresponding wires 375, to the connection box 305. The connection box 305, in some embodiments, may use the electric signals received from two or more electrodes to determine the differential signals between two or more individual electrodes (e.g., as described below with reference to FIG. 9B).

The ECG monitor 110, in some embodiments, may be a legacy (or conventional) ECG monitor. The ECG monitor 110 may include several input ports 325. The ECG monitor 110 may be configured to correctly process signals from the electrode patches 311-320 when each input port 325 receives a signal from an electrode patch that is placed at a specific location on the body of the person 190.

Similar to the cardiac monitoring system 100 of FIG. 1, the cardiac monitoring system 300 may store the expected signal profiles of the electrodes placed at specific positions on the body. Each expected signal profile may correspond to a position code. The expected signal profile may be identified by performing experiments to identify and learn the expected profile (e.g., the shape and or the contours) of the signals received from the electrodes that are placed at each specific position on the body.

The connection box 305 may include several input ports 307 and several output ports 308. Each wired electrode 311-320 may be attached to a specific input port of the connection box 305. Each output port of the connection box 305 may be connected to a specific input port 325 of the ECG monitor 110. The connection box 305 may include a processor (shown in FIGS. 9A-9B) that may compare the profile of the signals received from the wired electrodes 311-320 with the expected signal profiles. The processor of the connection box 305 may determine whether the wired electrodes 311-320 are placed on the corresponding expected positions on the body of the person 190 based on the comparison of the profile of the signals received from the wired electrodes with the expected signal profiles. The processor of the connection box may identify the actual position of any electrode that is placed on a wrong body position based on the profile of the signal received from the electrode.

Once the actual position of the wired electrodes 310-320 on the body 190 is determined, the connection box 305 may internally route the signals from the input ports 307 of the connection box to the output ports 308 of the connection box based on the actual positions of the electrodes on the body 190 such that the electrodes' signals are connected to the input terminals of the ECG monitor 110 based on the actual position of the electrode without requiring the electrodes that are positioned at wrong places on the body to be physically moved. Further details of the connection box are described below with reference to FIGS. 9A-9B.

Figure 4A:
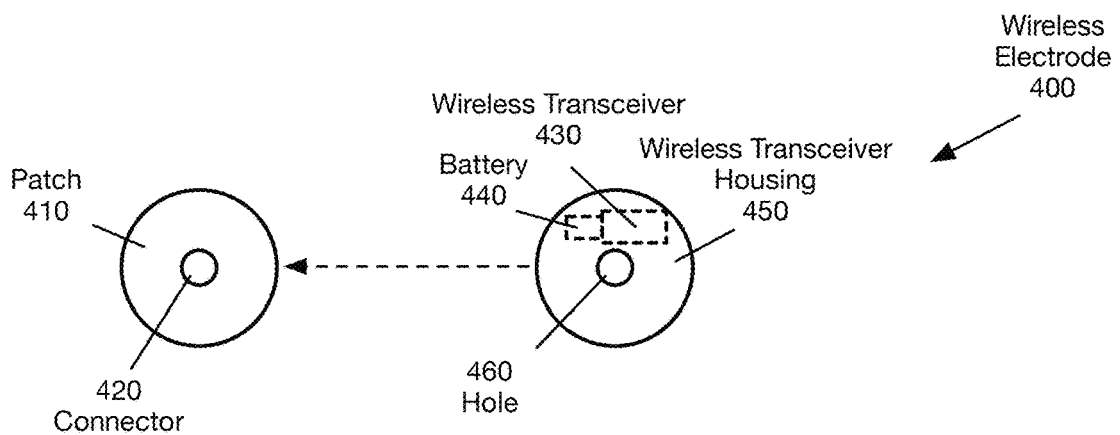
FIG. 4A is a top view and FIG. 4B is an elevational front view of a wireless electrode, according to various aspects of the present disclosure.
Figure 4B:
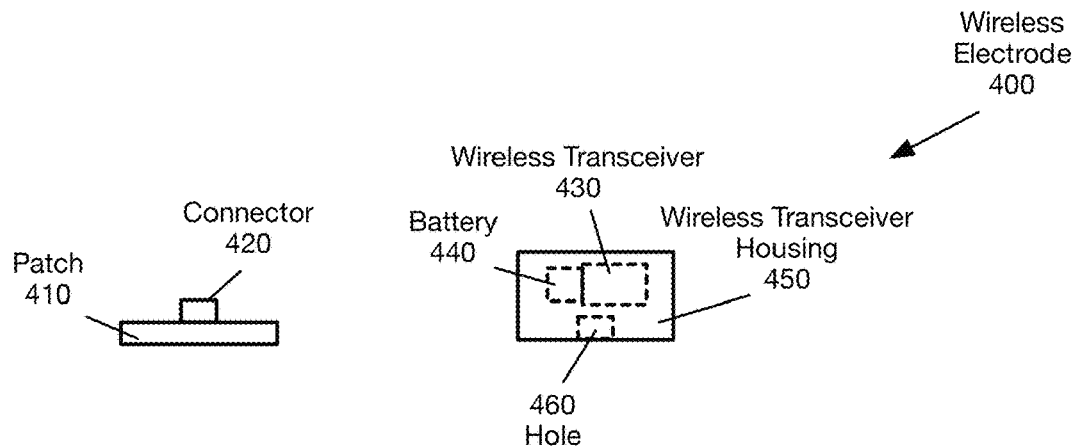
Figure 4C:
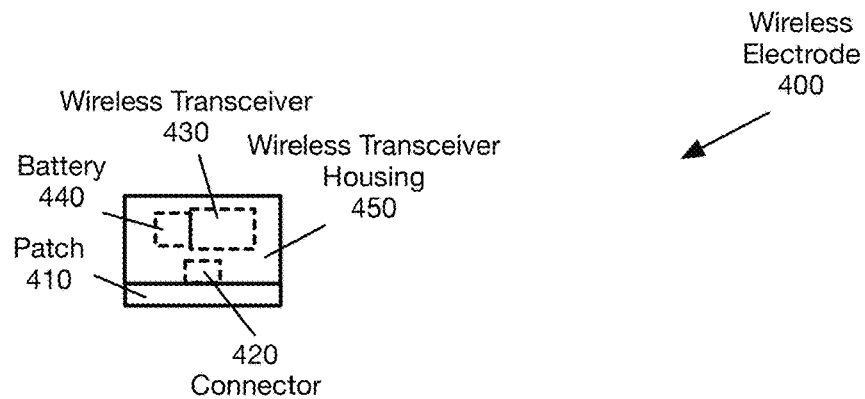
FIG. 4C is a front elevation view of the wireless electrode of FIGS. 4A-4B, after the patch and the wireless transceiver housing are connected to each other, according to various aspects of the present disclosure.

FIG. 4A is a top view and FIG. 4B is an elevational front view of a wireless electrode 400, according to various aspects of the present disclosure. FIG. 4C is a front elevation view of the wireless electrode of FIGS. 4A-4B, after the patch and the wireless transceiver housing are connected to each other, according to various aspects of the present disclosure.

With reference to FIGS. 4A-4C, the wireless electrode 400 may be any of the wireless electrodes 111-120 of FIGS. 1-2. The wireless electrode 400 may include a conductive patch 410 and a connector 420. The patch 410 may be a legacy (or conventional) patch commonly used for ECG testing. For example, the patch 410 may be similar to any of the patches 311-312 of FIG. 3. The conductive patch 410 may receive electrical signals from a person's heart when the patch is attached to the person's skin.

The patch 410 may include a placement designator, such as, a unique label and/or may have a unique color to assist in proper positioning of the electrode on the body. The wireless electrode 400 may include a wireless transceiver 430 and a battery 440. The battery 440 and the wireless transceiver 430, in some embodiments, may be inside a housing 450. The housing 450 may be attached to the electrode patch by the connector 420. For example, and without limitations, the connector 420 may be a pin and the housing 450 may include a hole 460 that matches the pin.

The electrode patch 410 and the connector 420, in some embodiments, may be disposable, and the wireless transceiver 430, the battery 440, and the housing 450 may be reusable. In order to preserve the battery 440, some embodiments may turn on the power to the transceiver 430 only after the battery 440 and the transceiver 430 are connected to the connector 420. For example, the connector 420 may act as a switch to turn the battery 440 on when the housing 450 is connected to the connector 420 and may turn off the battery 440 when the housing 450 is disconnected from the connector 420.

Figure 4D:
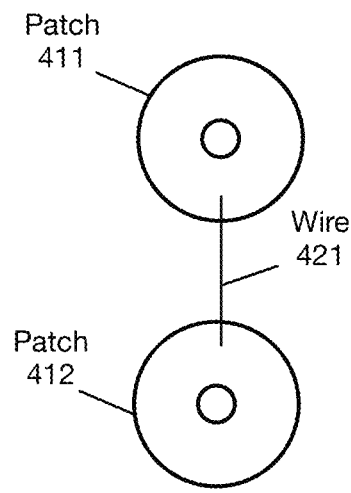
FIGS. 4D and 4E are functional diagrams illustrating two electrode patches connected by wire, according to various aspects of the present disclosure.
Figure 4E:
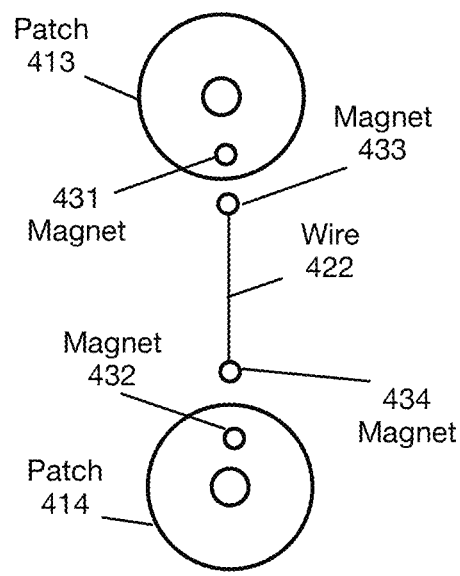

In the embodiments where it may be desired to directly sense the differential signal between two individual wireless electrodes, a physical connection via a short wire may be made between two or more electrodes. FIGS. 4D and 4E are functional diagrams illustrating two electrode patches connected by wire, according to various aspects of the present disclosure.

In the example of FIG. 4D, the two patches 411 and 412 may be permanently connected to each by the wire 421. In other embodiments the wires may be connected individually between the desired electrode pairs after placing the electrodes on the subject's body. In the example of FIG. 4E, the two patches 413 and 414 may include the magnets 431 and 432, respectively. The wire 422 may include one of the magnets 433 and 434 at each end. During operation, the patches 413 and 414 may be connected to each other, for example, by connecting the magnet 433 to the magnet 431, and the magnet 434 to the magnet 432. For ease of operation, the wires may be color coded to avoid mistakes. For example, the wire that connects a red-colored electrode patch to a green-colored electrode patch may be identified with red color on one end and green color on the opposite end.

Either one of the wireless electrodes that are connected to each other by wire may be assigned to perform the differential sensing and transmission via the circuits already integrated in all electrodes. For measuring multiple differential signals between multiple sets of wireless electrode pairs, multiple short wire connections may be made. The sensed differential signal may be digitized and wirelessly transmitted to the preprocessing unit 135 of FIG. 1 via the circuitry integrated inside the electrodes for further processing.

Figures 5, 6:
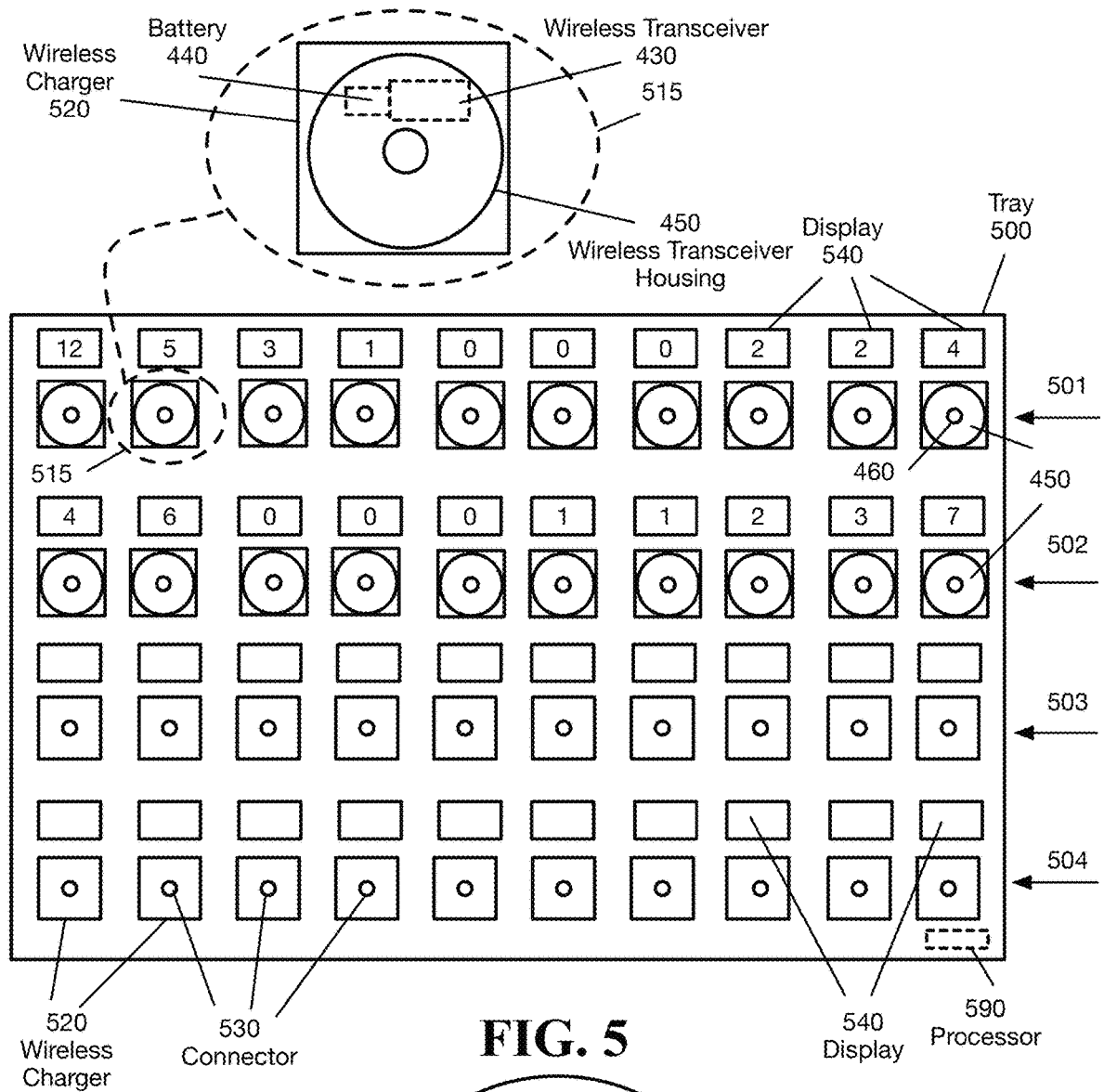
FIG. 5 is a functional diagram of one example embodiment of a tray for wirelessly charging batteries of wireless transceivers, according to various aspects of the present disclosure.
FIG. 6 is a top view of a housing of a wireless transceiver of a wireless electrode that includes a display, according to various aspects of the present disclosure.

Some embodiments may provide a tray to place the wireless transceiver housings while the batteries and wireless transceivers are not in use. The tray, in some embodiments, may include chargers to wirelessly charge the batteries inside the wireless transceivers' housings. FIG. 5 is a functional diagram of one example embodiment of a tray 500 for wirelessly charging batteries of wireless transceivers, according to various aspects of the present disclosure.

With reference to FIG. 5, the tray 500 may include several wireless chargers 520 to wirelessly charge the batteries that are inside the housings 450 of the wireless transceivers 430. In the depicted example, the tray 500 includes several rows 501-504 of wireless chargers 520. Each wireless charger 520 may include a connector 530 that may match the hole 460 of the wireless transceivers' housings 450 to hold the rechargeable battery of a wireless transceiver that is being charged in close vicinity of the wireless charger. In the example of FIG. 5, the wireless chargers 520 in the top two rows 501-502 of the tray 500 are connected to the housings 450 of wireless transceivers and the wireless chargers 520 in the bottom two rows 503-504 of the tray 500 are not connected to any wireless transceiver housings 440.

As shown by the expanded view 515, a wireless transceiver housing 450 may be connected to a wireless charger 520, and the battery 440 of the wireless transceiver 430 may wirelessly be charged by the wireless charger 520. The wireless charges 520, in some embodiments, may use resonant electromagnetic induction to charge the batteries of the wireless transceivers. In these embodiments, the chargers 520 may include coils for inducing electromagnetic power and the wireless electrodes may include a coil (e.g., inside the housing 450). The wireless chargers 520 may apply an alternating current (AC) to its coil, thereby creating an alternative magnetic field. This magnetic field may generate a voltage across the wireless electrode's coil, which may be rectified and smoothed with capacitors, and used for charging the wireless electrode's battery.

The wireless chargers 520, in some embodiments, may use radio frequency (RF) to charge the batteries. In these embodiments, the charger 520 may include an RF antenna and the wireless electrode may include an RF antenna. The RF antenna of the wireless electrode may be the same antenna that is used for communicating with the external electronic devices, such as, the ECG monitor 110 of FIG. 1 (e.g., through the wireless transceiver 140) or the mobile device(s) 160. Alternatively, the wireless electrodes may include an additional antenna inside the housing 450 that may be used to receive RF power from the wireless chargers. The antenna of the charger 520 may transmit RF power to the antenna of the wireless electrode. The received RF power may be converted electrical current and may be used to charge the battery of the wireless electrode.

In some embodiments, the tray 500 may include a display 540 associated with each wireless charger 520. The tray may include a processor 590 that may display the charge level of the battery of the housing 450 that is connected to the corresponding wireless charger 520 on the display 540 of the wireless charger 520. For example, the display 540 (as shown) may indicate how many more ECG runs a battery may handle. Alternatively, the display may indicate the charge level percentage of the battery.

In some embodiments, the battery and transceiver housing may include a small display that may display how many more ECG runs the battery may handle or the charge level percentage of the battery. FIG. 6 is a top view of a housing 450 of a wireless transceiver of a wireless electrode that includes a display, according to various aspects of the present disclosure. With reference to FIG. 6, the display 610 may indicate the charge level of the battery of the housing 450. For example, the display 610 may indicate how many more ECG runs a battery inside the housing 450 may handle. Alternatively, the display 610 may indicate the charge level percentage of the battery. The display 610, for example, may include a liquid-crystal display (LCD) or light-emitting diode (LED) lights.

Figure 7:
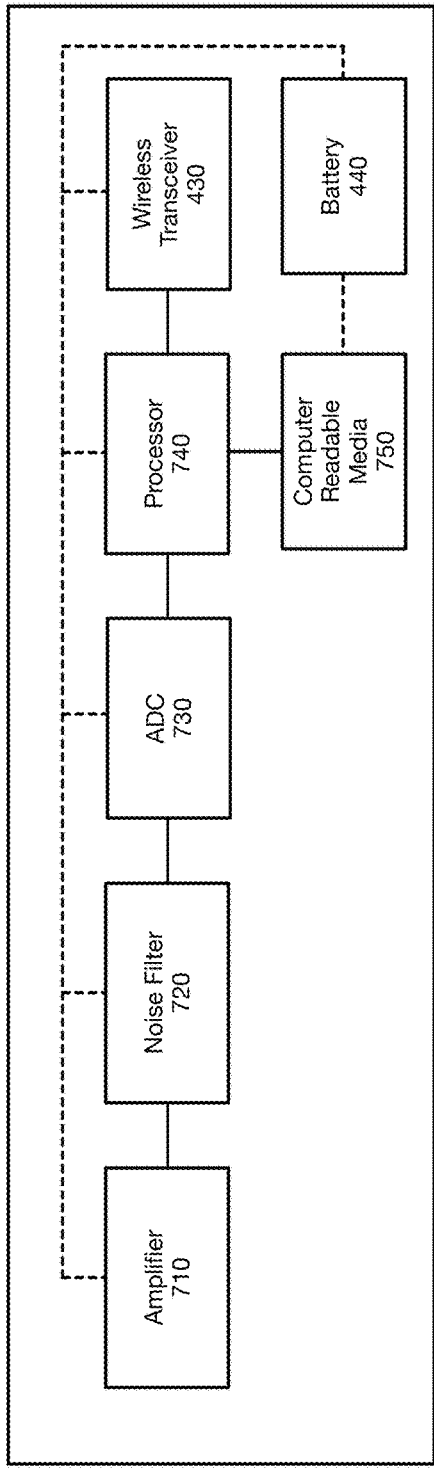
FIG. 7 is a functional block diagram illustrating the electronic components of a wireless electrode, according to various aspects of the present disclosure.

FIG. 7 is a functional block diagram illustrating the electronic components of a wireless electrode 400, according to various aspects of the present disclosure. With reference to FIG. 7, the wireless electrode 400, may be any of the wireless electrodes 111-120 of FIGS. 1-2 or the wireless electrode 400 of FIGS. 4-6. The wireless electrode 400 may include an amplifier 710, a noise filter 720, an analog to digital converter (ADC) 730, a processor 740, computer readable media 750, a wireless transceiver 430, and a battery 440.

The amplifier 710 may amplify the electric signal received from the heart by the conductive path 410 (FIGS. 4A-4C). The noise filter 720 may filter the noise from the amplified output signal of the amplifier 720. The ADC 730 may convert the analog output of the noise filter 720 to digital.

The processor 740 may be, for example, and without limitations, a microprocessor or a microcontroller. The computer readable media 750 may be volatile memory and non-volatile memory to store data and/or computer readable instructions.

The computer readable media 750 may store the position code of the wireless electrode 400. The position code may identify the location on a person's body that the wireless electrode 400 is expected to be placed during an ECG run. The processor 740 may store the digitized signals received from the heart in the computer readable media 750. The processor may retrieve the position code from the computer readable media 750 and include the position code in the digital data that is transmitted by the wireless transceiver 430. The processor 740 may execute code that is stored in the computer readable media 750. The processor 740, in some embodiments, may determine the charge level of the battery 440 and may display (e.g., on the display 610 of the wireless transceiver) the charge level of the battery, the percentage of the battery charge left, or the number of ECG runs a battery may handle with the current charge level.

Figure 8:
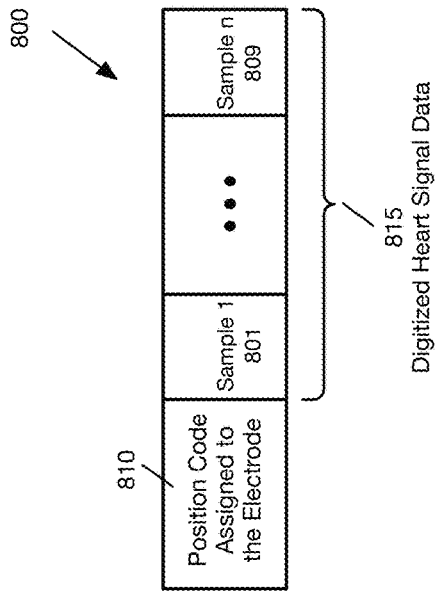
FIG. 8 is a functional diagram illustrating a data packet transmitted by a wireless electrode, according to various aspects of the present disclosure.

FIG. 8 is a functional diagram illustrating a data packet 800 transmitted by a wireless electrode, according to various aspects of the present disclosure. With reference to FIG. 8, the transmitted data packet 800 may be similar to any of the transmitted data 241-250 of FIG. 2. The transmitted data packet 800 may include the position code 810 that is assigned to the electrode and is stored in the computer media 750 of the electrode.

Since each electrode may have a visual identifier (e.g., a color, a name, etc.) to help an operator to correctly position the electrode on the body, the assigned position code correlates to the expected position of the electrode on the body. However, if a healthcare personnel makes a mistake and places the electrode at a wrong location on the body, the electrode still transmits the position code that is assigned to it (i.e., the position code that identifies the expect position and not the actual position of the electrode on the body).

The transmitted electrode data 800 may include the digitized heart signal data 815. In the example of FIGS. 7 and 8, the digitized heart signal data 815 may be the output of the ADC 730. The sampling rate of the ADC 730 may be predetermined or programmable. For example, the processor 740 may set the sampling rate the ADC 730. As an example, the sampling rate may be a multiple (e.g., and without limitations, 10-1000 times) of a typical person's heart rate. The processor 740 may receive the output of the ADC 730.

The processor 740 may store digitized heart signal samples received by the electrode at several different times in the computer readable media 750 and may transmit them together. For example, the digitized heart signal data 815, in some embodiments, may include the digitized data associated with several samples 801-809 of the heart electrical signal received by the electrode. The samples 801-809 may be taken during a fraction of a heartbeat, during one heartbeat, or during more than one heart beats. The preprocessing unit 135 (FIG. 1) may use the samples 801-809 received in several packets 800 to generate the profile of the signal the is received by the electrode 400.

Referring back to FIG. 7, the battery 440 may be similar to the battery 440 of FIGS. 4A-4C, 5, and 6. The battery 440 may provide power to the electronic components of the wireless electrode 430. The wireless transceiver 430 may be similar to the wireless transceiver of FIGS. 4A-4C and 5. The wireless transceiver 430 may wirelessly transmit the digitized heart signal and the identification code of the wireless electrode 430.

Figure 9A:
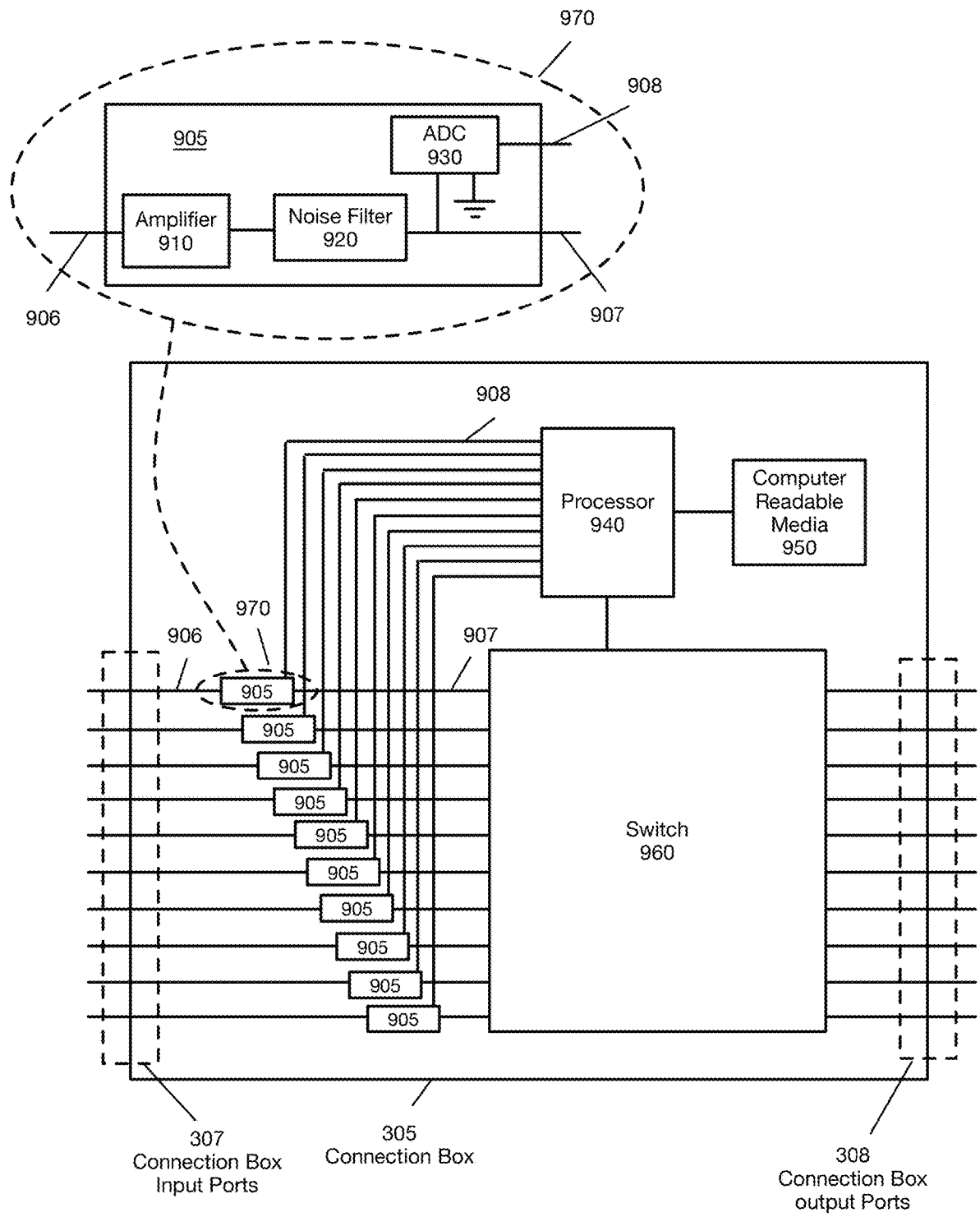
FIG. 9A is a functional block diagram illustrating the electronic components of a connection box, according to various aspects of the present disclosure.

FIG. 9A is a functional block diagram illustrating the electronic components of a connection box 305, according to various aspects of the present disclosure. With reference to FIG. 9A, the connection box 305 may be similar to the connection box 305 of FIG. 3. The connection box 305 may include a processor 940, computer readable media 950, and a switch 960.

The connection box 305 may receive analog heart signals from the wired electrodes 311-320 (FIG. 3) at the input ports 307 of the connection box 305. The connection box 305 may include electronic circuitry 905 for converting and conditioning signals received at each input port 307 of the connection box 305. As shown by the expanded view 970, each electronic circuitry 905 may include an amplifier 910, a noise filter 920, and an ADC 930.

Each amplifier 910 may receive an analog signal from a wired electrode at the input port 906 of the corresponding electronic circuitry 905. The amplifier 910 may amplify the electric signal received from the heart by the conductive patch 410 (FIGS. 4A-4C) of the corresponding electrode. The noise filter 920 may filter the noise from the amplified output signal of the amplifier 920. One output 907 of each electronic circuitry may be connected to an input port of the switch 960. The ADC 930 may convert the analog output of the noise filter 920 to digital. The output 908 of each ADC may be connected to the processor 940.

The processor 940 may be, for example, and without limitations, a microprocessor or a microcontroller. The computer readable media 950 may be volatile memory and/or non-volatile memory to store data and/or computer readable instructions. The processor 940 may store the digitized signals received from the ADCs 930 in the computer readable media 950.

The processor 940 may compare the profile of the signals received from the heart by the electrodes with the expected signal profiles and may determine whether the wired electrodes 311-320 (FIG. 3) are placed on the corresponding expected positions on the body of the person 190. The processor 940 may identify the actual position of any electrode that is placed on a wrong body position based on the profile of the signal received from the electrode.

Once the actual position of the wired electrodes 310-320 on the body 190 is determined, the processor 940 may program the switch 960 to internally route the analog signals received from the input ports 307 of the connection box to the output ports 308 of the connection box based on the actual positions of the electrodes on the body such that the electrodes' signals are connected to output ports 308 of the connection box as expected by the ECG monitor 110 (FIG. 3).

Figure 9B:
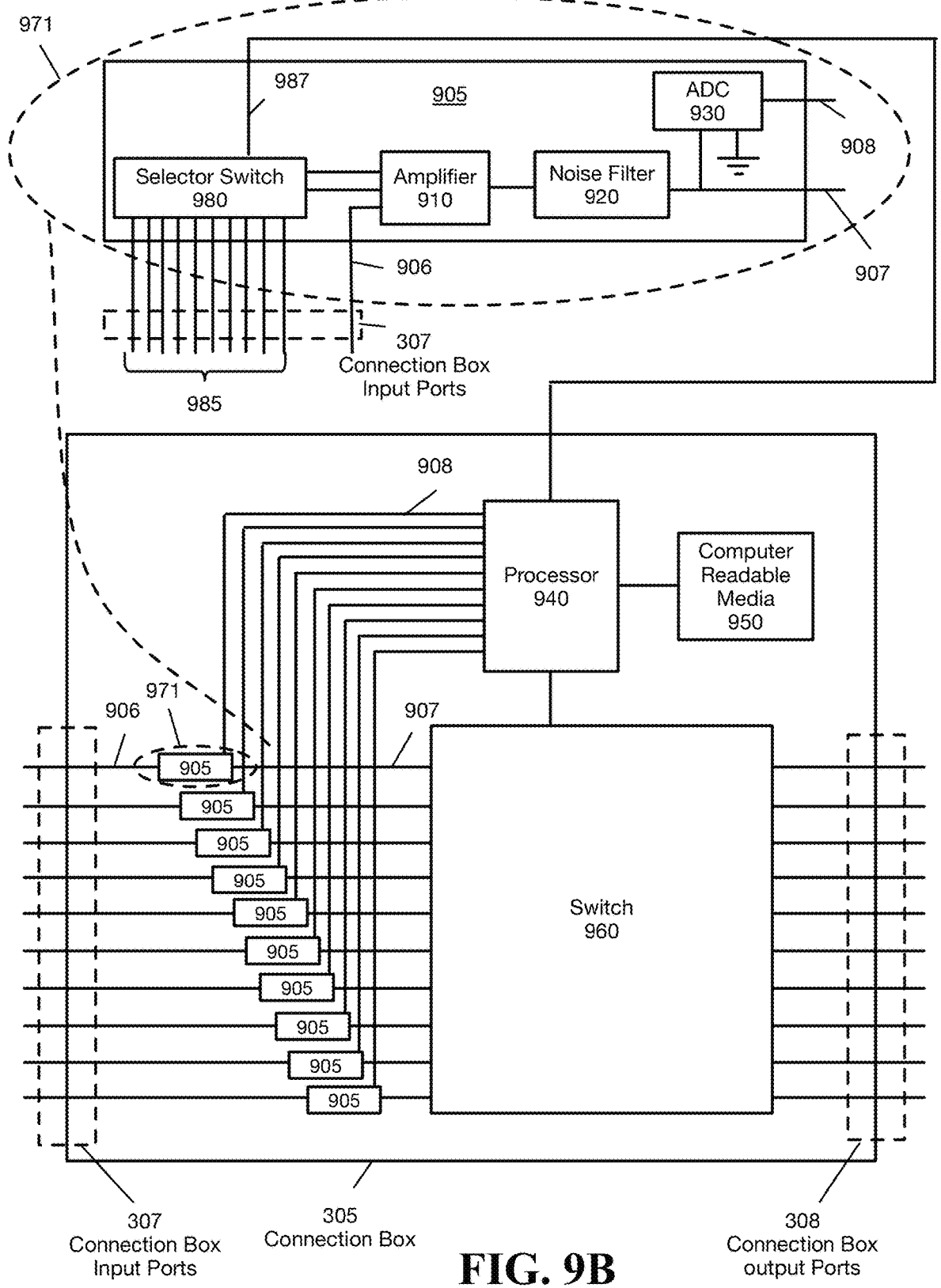
FIG. 9B is a functional block diagram illustrating an alternative design of the electronic circuitry of the connection box that generates a differential signal between two or more individual wireless electrodes, according to various aspects of the present disclosure.

In some embodiments the outputs 907 and 908 of the electronic circuitry 905 of the connection box 305 may be a differential signal between two or more individual wireless electrodes. FIG. 9B is a functional block diagram illustrating an alternative design of the electronic circuitry 905 of the connection box 305 that generates a differential signal between two or more individual wireless electrodes, according to various aspects of the present disclosure. With reference to FIG. 9B, each electronic circuitry 905 of FIG. 9B may include a selector switch 980. As shown by the expanded view 971, the input 906 to the amplifier 910 may directly come from one of the connection box input ports 307. The other connection box input ports of the connection box may be routed to the inputs 985 of the selector switch 980. The control line 987 of the selector switch 980 may be connected to the processor 940. The processor 940 may program the selector switch to selectively route one of more inputs 985 through the output 988 of the selector switch 980 into the input of the amplifier 910. The processor 940 may also program the selector switch not to route any of the inputs 985 to the inputs of the amplifier 910.

Figure 10:
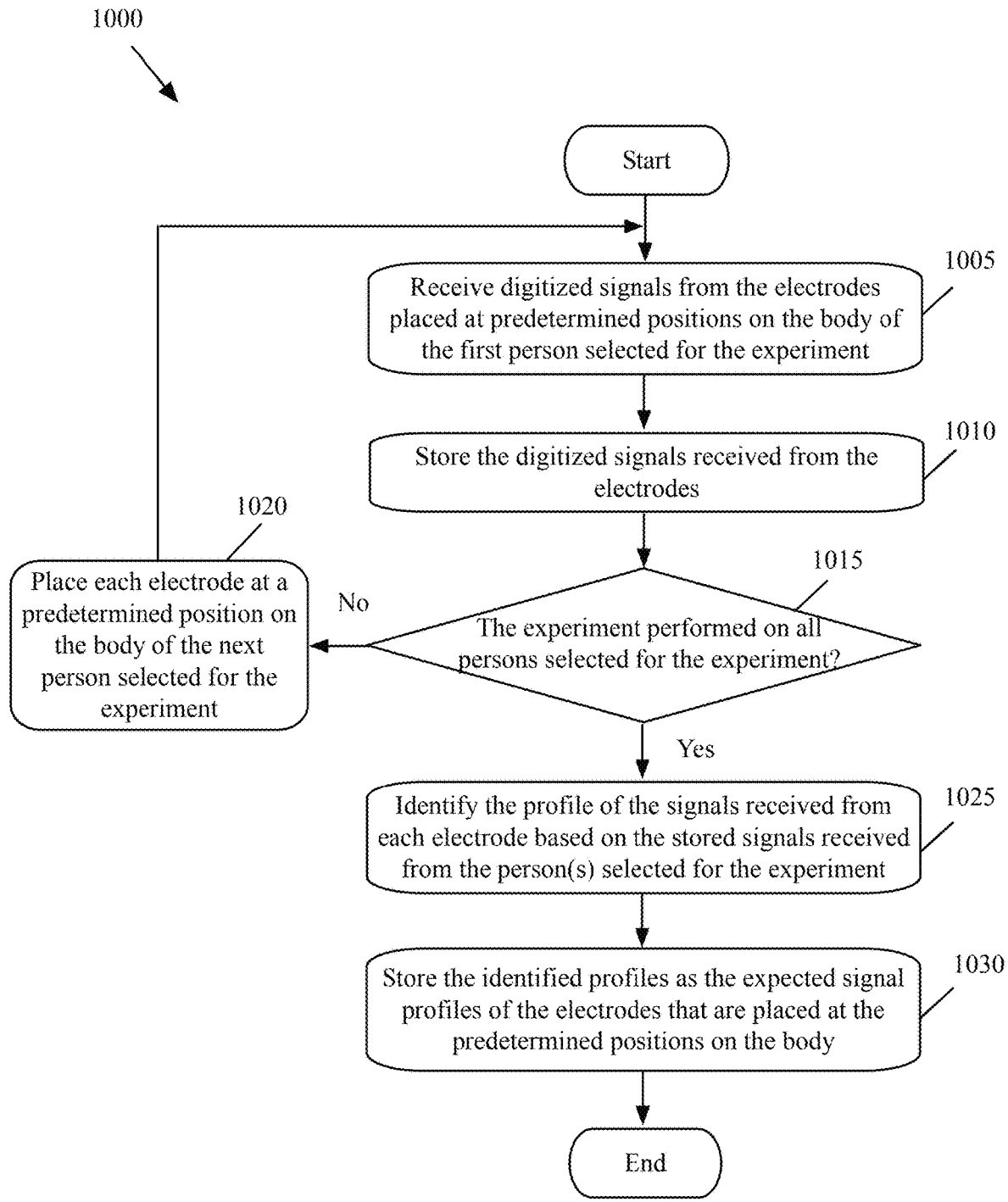
FIG. 10 is a flowchart illustrating an example process for determining the expected signal profiles of the electrodes that are placed at predetermined positions on the body, according to various aspects of the present disclosure.

Some embodiments may perform experiments to identify and learn the expected profile, for example the shape and contour, of the signals received from the electrodes that are placed at each specific position on the body. The experiments may be performed by placing the electrodes on the body of one or more persons that are selected for the experiment. FIG. 10 is a flowchart illustrating an example process 1000 for determining the expected signal profiles of the electrodes that are placed at predetermined positions on the body, according to various aspects of the present disclosure. The process 1000, in some of the present embodiments, may be performed by a processor of a computing device that may be used to identify and store the signal profiles.

With reference to FIG. 10, digitized signals may be received (at block 1005) from the electrodes placed at predetermined position on the body of the first person selected for the experiment. For example, the heart signal received from electrodes may be digitized by an ADC and the output of the ADC may be received by the processor of the electronic device that is performing the process 1000. The digitized signals may be stored (at block 1010).

A determination may be made (at block 1015) whether the experiment is performed on all persons selected for the experiment. If yes, the process 1000 may proceed to block 1025, which is described below. If not, each electrode may be placed (at block 1020) at a predetermined position on the body of the next person selected for the experiment. The process 1000 may then proceed to block 1005, which was described above.

When it is determined (at block 1015) that the experiment is performed on all selected persons, the profile of the signals received from each electrode may be identified (at block 1025) based on the stored signals received from the person(s) selected for the experiment. The profile of the signals may include, for example, and without limitations, the shape or the contour of the signals.

The identified profiles may be stored (at block 1030) as the expected signal profiles of the electrodes that are placed at the predetermined positions on the body. The process 1000 may then end. Some embodiments may use the expected signal profiles identified by of the experiment to identify the electrodes that are placed at wrong positions on the body and change the position code of the electrode data to the position code corresponding the actual position of the electrode.

Figure 11:
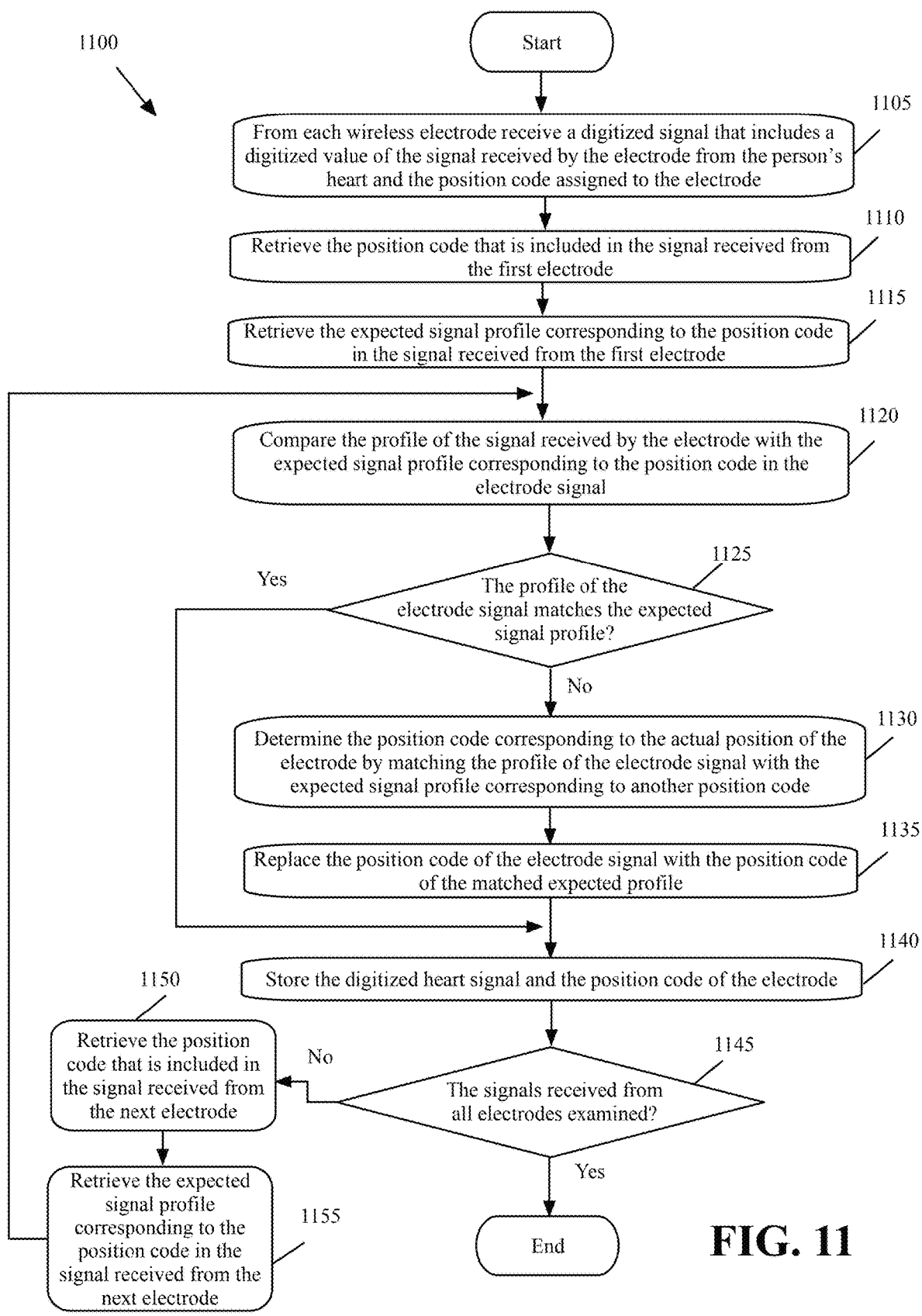
FIG. 11 is a flowchart illustrating an example process for identifying the electrodes that are placed at wrong positions on the body and changing the position code in the data transmitted by the electrode to the position code corresponding the actual position of the electrode, according to various aspects of the present disclosure.

FIG. 11 is a flowchart illustrating an example process 1100 for identifying the electrodes that are placed at wrong positions on the body and changing the position code in the data transmitted by the electrode to the position code corresponding the actual position of the electrode, according to various aspects of the present disclosure. The process 1100, in some of the present embodiments, may be performed by a processor of the wireless cardiac monitoring system 100 of FIG. 1 (e.g., by a processor of the preprocessing unit 135 or a processor of the ECG monitor 110 in the embodiments that the preprocessing unit does not have a processor).

With reference to FIG. 11, from each wireless electrode a digitized signal may be received (at block 1105) that includes a digitized value of a signal received by the electrode from the person's heart and the position code assigned to the electrode. For example, a transmitted digital signal such as the transmitted packet 800 of FIG. 8 may be received by the preprocessing unit 135 of FIG. 1. The position code that is included in the signal received from the first electrode may be retrieved (at block 1110). For example, the position code 810 (FIG. 8) included in the packet 800 transmitted by the electrode may be retrieved from the transmitted data.

The expected signal profile corresponding to the position code in the signal received from the first electrode may then be retrieved (at block 1115). For example, the expected signal profile for the position code of the electrode that was identified by the experiment, as described above with reference to FIG. 10, may be retrieved from a database.

The profile of the signal received by the electrode may be compared (at block 1120) with the expected signal profile corresponding to the position code in the electrode signal. A determination may be made (at block 1125) whether the profile of the electrode signal matches the expected signal profile. If yes, the process 1100 may proceed to block 1140, which is described below.

Otherwise, the position code corresponding to the actual position of the electrode may be determined (at block 1130) by matching the profile of the electrode signal with the expected signal profile corresponding to another position code. The position code in the digitized signal of the electrode may then be replaced (at block 1135) with the position code of the matched signal profile. For example, the position code of in the digitized signal of the electrode may be received with the position code of the actual location of the electrode as described with reference to stage 202 of FIG. 2.

At block 1140, the digitized heart signal and the position code corresponding to the actual position of the electrode may be stored. A determination may be made (at block 1145) whether the signals received from all electrodes are examined. If yes, the process 1100 may end.

Otherwise, the position code that is included in the signal received from the next electrode may be retrieved (at block 1150). The expected signal profile corresponding to the position code in signal received from the next electrode may be retrieved (at block 1155). The process 1100 may then proceed to block 1120, which was described below.

Figure 12:
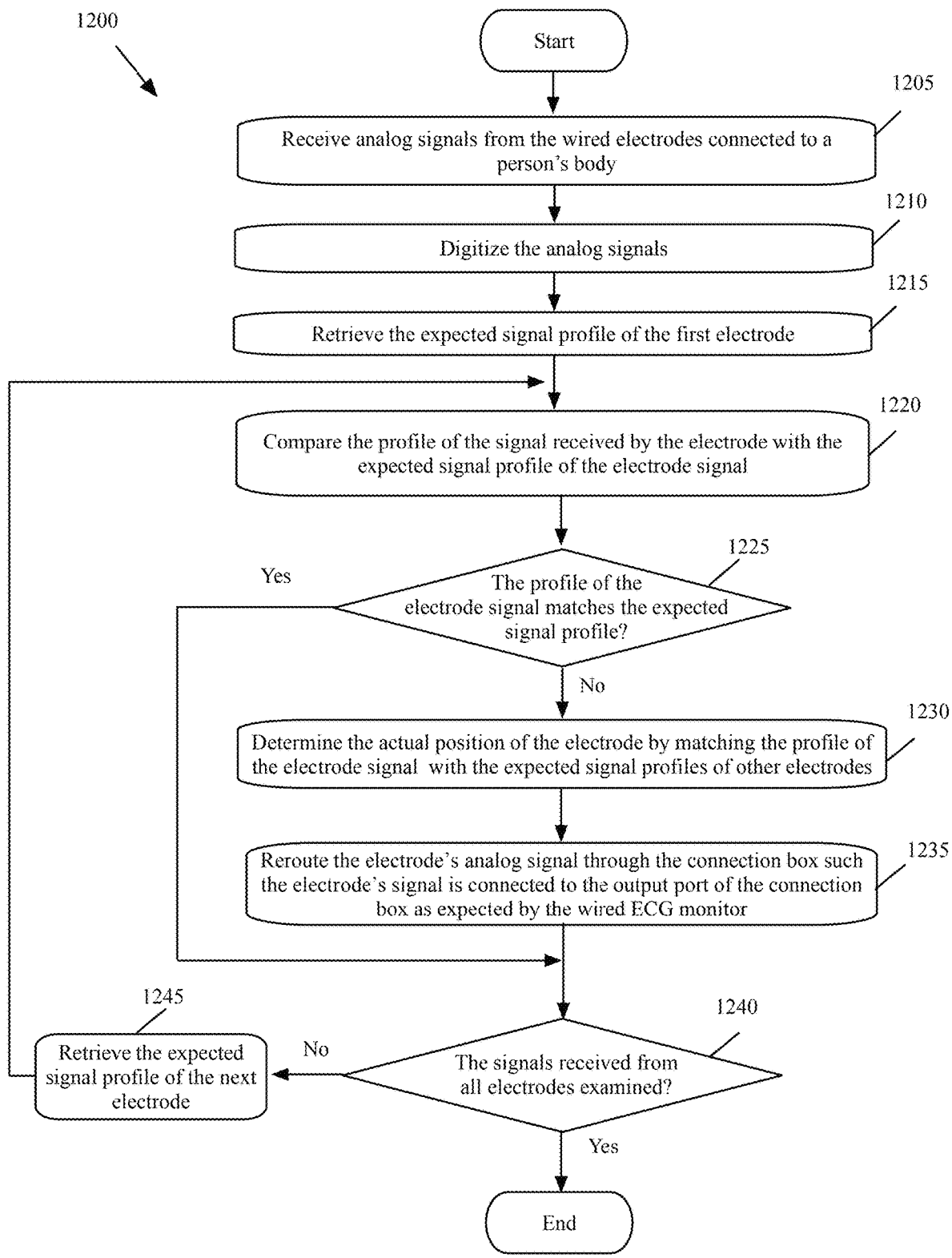
FIG. 12 is a flowchart illustrating an example process for identifying the wired electrodes that are placed at wrong positions on the body and rerouting the analog signal received from the electrode to an input port of a wired cardiac monitoring system, according to various aspects of the present disclosure.

FIG. 12 is a flowchart illustrating an example process 1200 for identifying the wired electrodes that are placed at wrong positions on the body and rerouting the analog signal received from the electrode to an input port of a wired cardiac monitoring system, according to various aspects of the present disclosure. The process 1200, in some of the present embodiments, may be performed by a connection box 305 of the wired cardiac monitoring system 300 of FIG. 3.

With reference to FIG. 12, analog signals from the wired electrodes connected to a person's body may be received (at block 1205). For example, the analog signals from the electrode patches 311-320 of FIG. 3 may be received through the wires 375 at the connection box 305. The analog signal may be digitized (at block 1210). For example, the analog signal may be digitized by the ADCs 930 of the electronic circuitries 905 and the digitized signals may be received by the processor 940 of the connection box 305 as shown in FIGS. 9A-9B.

The expected signal profile of the first electrode may then be retrieved (at block 1215). For example, the expected signal profile for first electrode that was identified by the experiment, as described above with reference to FIG. 10, may be retrieved from a database.

The profile of the signal received by the electrode may be compared (at block 1220) with the expected signal profile of the electrode. A determination may be made (at block 1225) whether the profile of the electrode signal matches the expected signal profile. If yes, the process 1200 may proceed to block 1240, which is described below.

The electrode's analog signal may be rerouted (at block 1235) through the connection box such the electrode's signal is connected to the output port of the connection box as expected by the wired ECG monitor. At block 1240, a determination may be made whether the signals received from all electrodes are examined. If yes, the process 1200 may end. Otherwise, the expected signal profile corresponding to the next electrode may be retrieved (at block 1250). The process 1200 may then proceed to block 1220, which was described below.

In some embodiments, the electrodes (either wired or wireless electrodes) may have a visual indicator (e.g., color, tag, etc.) that identify the expected position of the electrode on the body. Some of these embodiments may require one or more color images to be taken from the electrodes that are placed on a person's body. The color image(s) of the electrodes placed on the body may be analyzed by a processor of the cardiac monitoring system to determine whether the electrodes are correctly placed on the body. Since each electrode with a visual identifier (e.g., a color code) has to be placed at a predetermined position on the body, any electrode that is incorrectly positioned may be identified when the actual position of a color-coded electrode does not match the expected position of the electrode.

Figure 13:
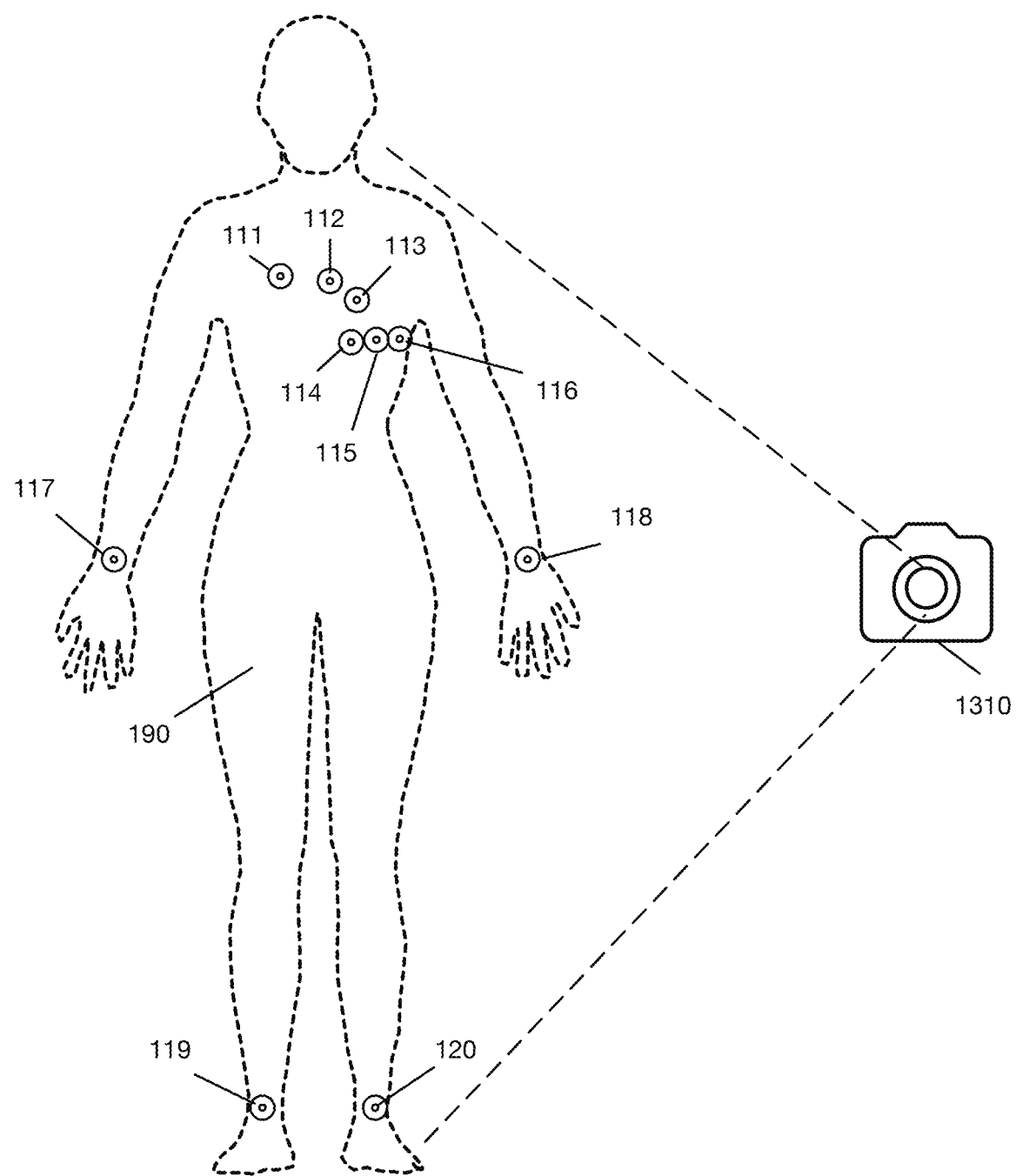
FIG. 13 is a functional diagram illustrating a camera taking color images of wireless electrodes connected to a person's body, according to various aspects of the present disclosure.

FIG. 13 is a functional diagram illustrating a camera taking color images of wireless electrodes connected to a person's body, according to various aspects of the present disclosure. As shown in FIG. 13, a camera 1310 may be used to take one or more color images of the wireless electrodes 111-120 that are placed on the body of a person 190. The camera 1310 may be a standalone camera, or the camera of a mobile device, such as a smartphone. The camera 1310 may have resolution that is higher than a threshold. The images taken by the camera 1310 may be sent to the preprocessing unit 135 of the wireless cardiac monitoring system 80 of FIG. 1 for analysis.

Figure 14A:
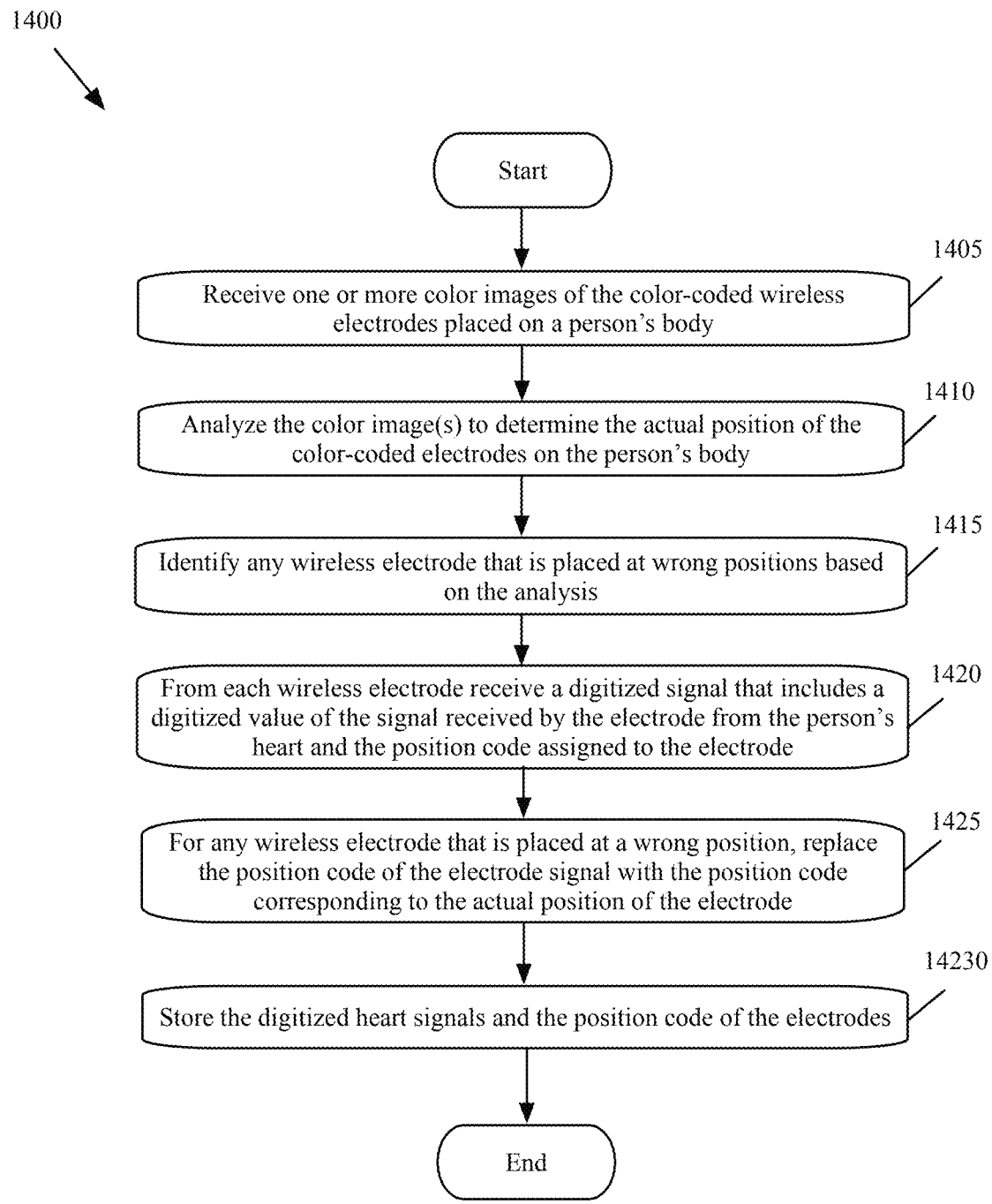
FIG. 14A is a flowchart illustrating an example process for identifying the wireless electrodes that are placed at a wrong position on the body by analyzing color images and changing the position code in the data transmitted by the electrode to the position code corresponding the actual position of the electrode, according to various aspects of the present disclosure.

FIG. 14A is a flowchart illustrating an example process 1400 for identifying the wireless electrodes that are placed at wrong positions on the body by analyzing color images and changing the position code in the data transmitted by the electrode to the position code corresponding the actual position of the electrode, according to various aspects of the present disclosure. The process 1400, in some of the present embodiments, may be performed by a processor of the wireless cardiac monitoring system 100 of FIG. 1 (e.g., by a processor of the preprocessing unit 135 or a processor of the ECG monitor 110 in the embodiments that the preprocessing unit does not have a processor).

With reference to FIG. 14A, one or more color images of the color-coded wireless electrodes placed on a person's body may be received (at block 1405). For example, the camera 1310 of FIG. 13 may take one or more color images and send the color images to the wireless cardiac monitoring system 80 of FIG. 1.

The color image(s) may be analyzed (at block 1410) to determine the actual position of the color-coded electrodes on the person's body. For example, the color image(s) may be analyzed to identify the contour of the person's body, to identify the color-coded wireless electrodes on the color image(s), and to identify the actual location of the color-coded wireless electrodes on the body.

Any wireless electrode that is placed at a wrong position on the body may then be identified (at block 1415) based on the analysis. For example, the actual position of the color-coded wireless electrodes that are determined from the analysis of the color image(s) may be compared by the expected position of the wireless electrodes that are stored in a database and identify the wireless electrodes that are located at wrong position on the body.

For each wireless electrode, a digitized signal that includes a digitized value of the signal received by the electrode from the person's heart and the position code assigned to the electrode may be received (at block 1420). For example, a transmitted digital signal such as the transmitted packet 800 of FIG. 8 may be received from each wireless electrode by the preprocessing unit 135 of FIG. 1.

For any wireless electrode that is placed at a wrong position, the position code of the electrode signal may be replaced (at block 1425) with the position code corresponding to the actual position of the electrode. For example, the position code of in the digitized signal of the electrode may be received with the position code of the actual location of the electrode as described with reference to stage 202 of FIG. 2. The digitized heart signals and the position codes corresponding to the actual positions of the electrode may be stored (at block 1430). The process 1400 may then end.

Figure 14B:
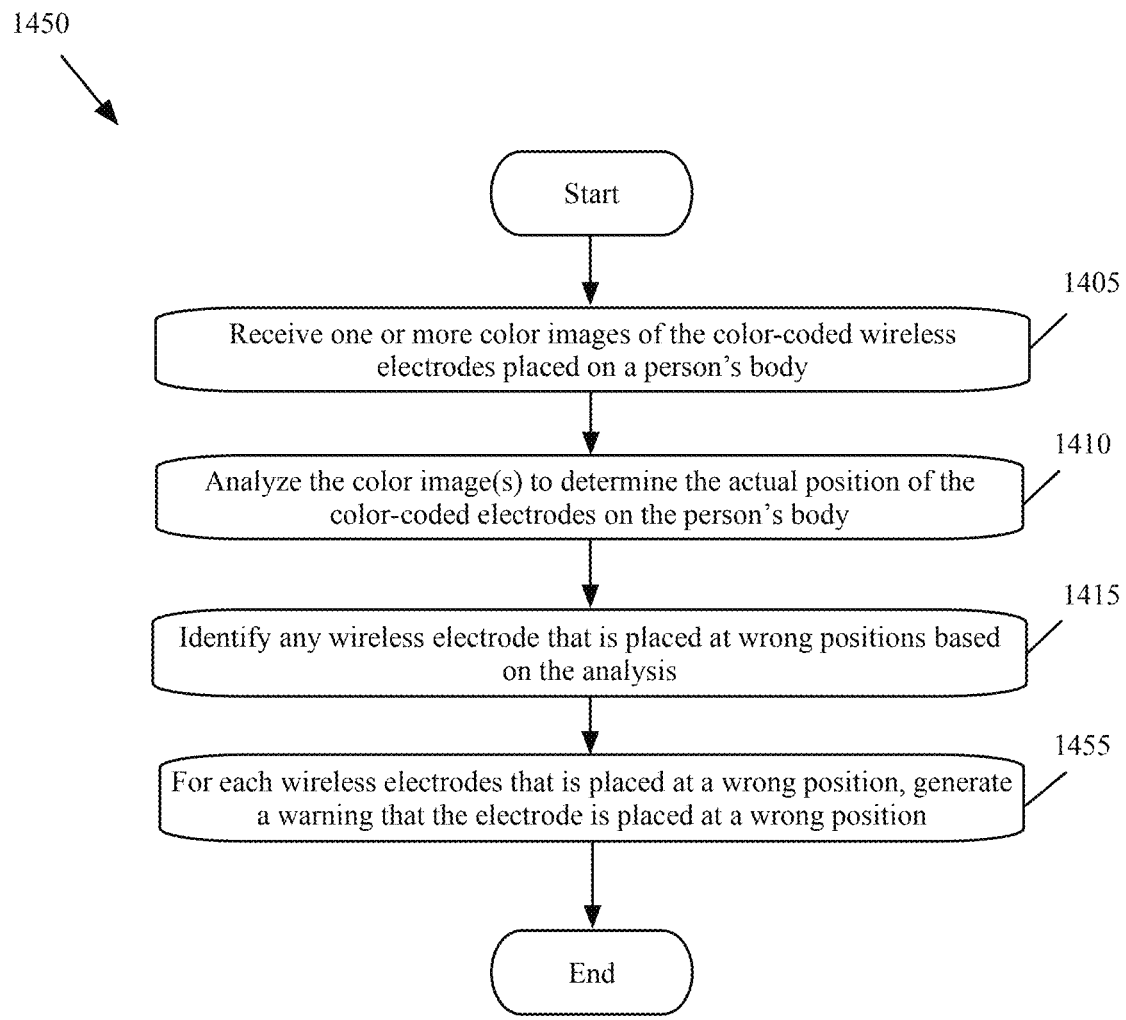
FIG. 14B is a flowchart illustrating an example process for identifying the wireless electrodes that are placed at a wrong position on the body by analyzing color images and generating a warning for each electrodes that is placed at a wrong position, according to various aspects of the present disclosure.

FIG. 14B is a flowchart illustrating an example process 1450 for identifying the wireless electrodes that are placed at a wrong position on the body by analyzing color images and generating a warning for each electrodes that is placed at a wrong position, according to various aspects of the present disclosure. The process 1450, in some of the present embodiments, may be performed by a processor of the wireless cardiac monitoring system 100 of FIG. 1 (e.g., by a processor of the preprocessing unit 135 or a processor of the ECG monitor 110 in the embodiments that the preprocessing unit does not have a processor).

With reference to FIG. 14B, blocks 1405-1415 may be similar to the corresponding blocks of FIG. 14A. The process 1450, for each wireless electrodes that is placed at a wrong position, may generate (at block 1455) a warning that the electrode is placed at a wrong position. The warning may be used by the health care personnel that are performing the ECG test. The warning may be in the form of an audio and/or a visual message. In addition to, or in lieu of the audio and/or the visual message, the wireless electrodes 111-120 may include a display or a light (e.g., one or more LEDs or a display, such as the display 610 shown in FIG. 6) that may blink when the process 1450 determines that the electrode is positioned at a wrong place to alert the medical health care personnel to correct the position of the wireless electrode. In some embodiments, the warning message may instruct the health care personnel to correct the position of the wireless electrodes that are placed at wrong positions. The message may identify the visual indicator of the electrodes that are placed at wrong positions. The process 1450 may then end.

Figure 15:
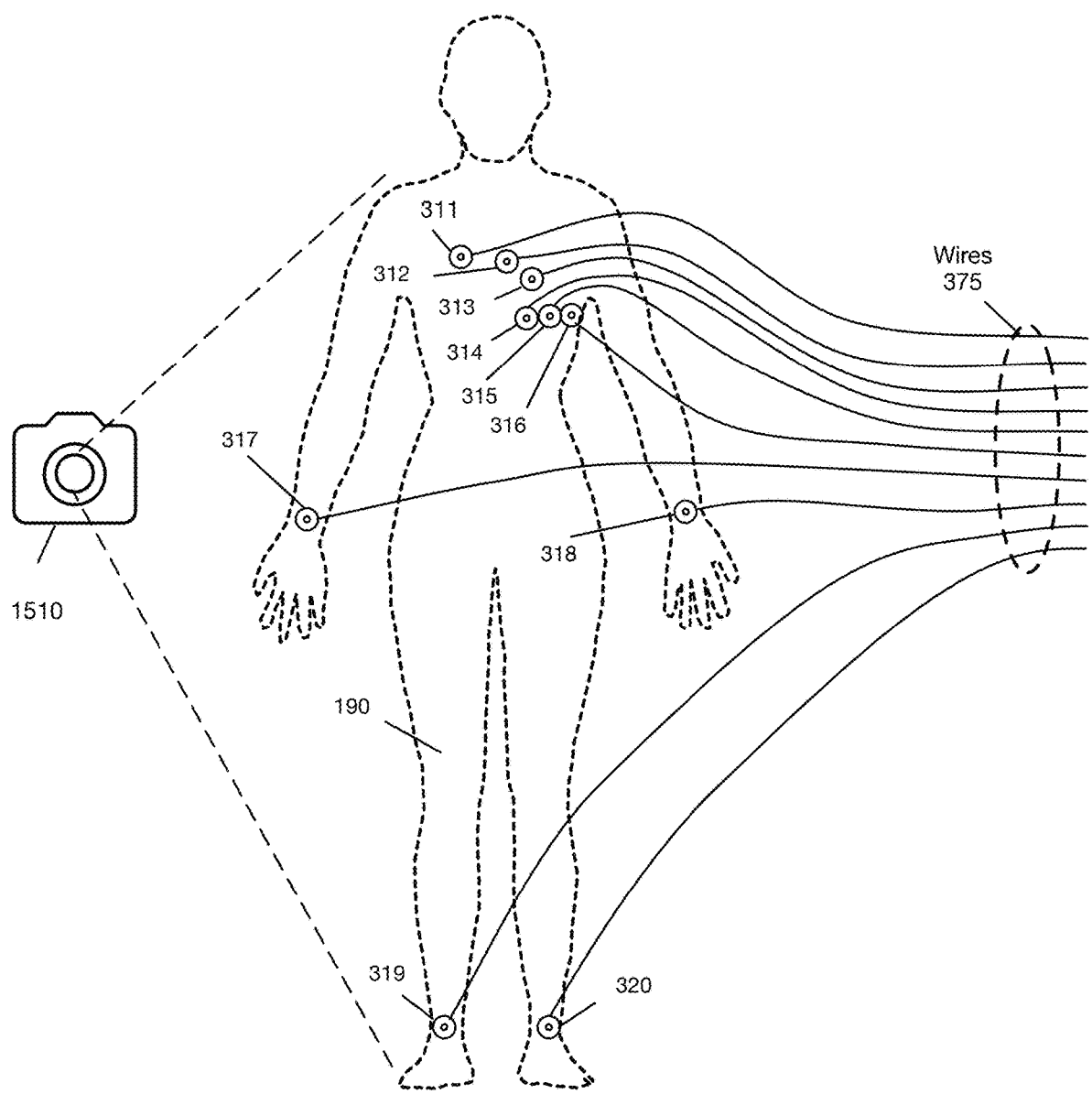
FIG. 15 is a functional diagram illustrating a camera taking color images of wired electrodes connected to a person's body, according to various aspects of the present disclosure.

FIG. 15 is a functional diagram illustrating a camera taking color images of wired electrodes connected to a person's body, according to various aspects of the present disclosure. As shown in FIG. 15, a camera 1510 may be used to take one or more color images of the wired electrodes 311-320 that are placed on the body of the person 190. The camera 1510 may have resolution that is higher than a threshold. The camera 1510 may be a standalone camera, or the camera of a mobile device, such as a smartphone. The images taken by the camera 1510 may be sent to the connection box 305 of the wired cardiac monitoring system 300 of FIG. 3 for analysis. It should be noted that the image(s) may be taken after the electrode patches 311-320 are placed on the body, either before or after the wires 375 are attached to the electrode patches 311-320.

Figure 16A:
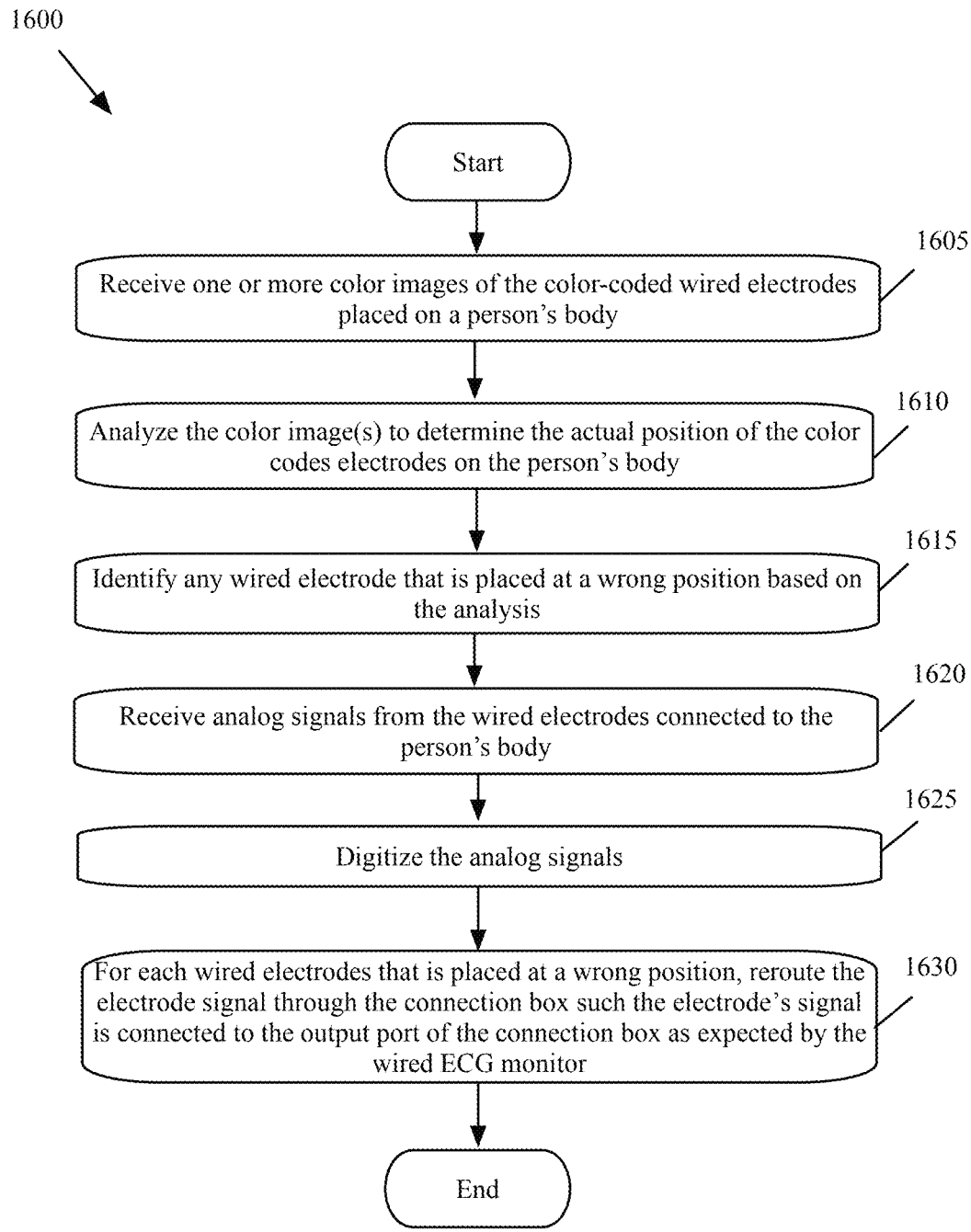
FIG. 16A is a flowchart illustrating an example process for identifying the wired electrodes that are placed at wrong positions on the body by analyzing color images and changing the position code in the data transmitted by the electrode to the position code corresponding the actual position of the electrode, according to various aspects of the present disclosure.

FIG. 16A is a flowchart illustrating an example process 1600 for identifying the wired electrodes that are placed at wrong positions on the body by analyzing color images and changing the position code in the data transmitted by the electrode to the position code corresponding the actual position of the electrode, according to various aspects of the present disclosure. The process 1600, in some of the present embodiments, may be performed by a processor of the connection box 305 of FIG. 3.

With reference to FIG. 16A, one or more color images of the color-coded wired electrodes placed on a person's body may be received (at block 1605). For example, the camera 1510 of FIG. 15 may take one or more color images and send the color images to the wired cardiac monitoring system 300 of FIG. 3.

The color image(s) may be analyzed (at block 1610) to determine the actual position of the color-coded electrodes on the person's body. For example, the color image(s) may be analyzed to identify the contour of the person's body, to identify the color-coded wireless electrodes on the color image(s), and to identify the actual location of the color-coded wireless electrodes on the body.

Any wired electrodes that is placed at a wrong position on the body may then be identified (at block 1615) based on the analysis. For example, the actual position of the color-coded wired electrodes that are determined from the analysis of the color image(s) may be compared by the expected position of the wireless electrodes that are stored in a database and identify the wireless electrodes that are located at wrong position on the body.

Analog signals may be received (at block 1620) from the wired electrodes connected to the person's body. For example, the analog signals from the electrode patches 311-320 of FIG. 3 may be received through the wires 375 at the connection box 305. The analog signal may be digitized (at block 1610). For example, the analog signal may be digitized by the ADCs 930 of the electronic circuitries 905 and the digitized signals may be received by the processor 940 of the connection box 305 as shown in FIGS. 9A-9B.

For each wired electrode that is placed at a wrong position, the electrode signal may be rerouted (at block 1630) through the connection box such the electrode's signal is connected to the output port of the connection box as expected by the wired ECG monitor. The process 1600 may then end.

Figure 16B:
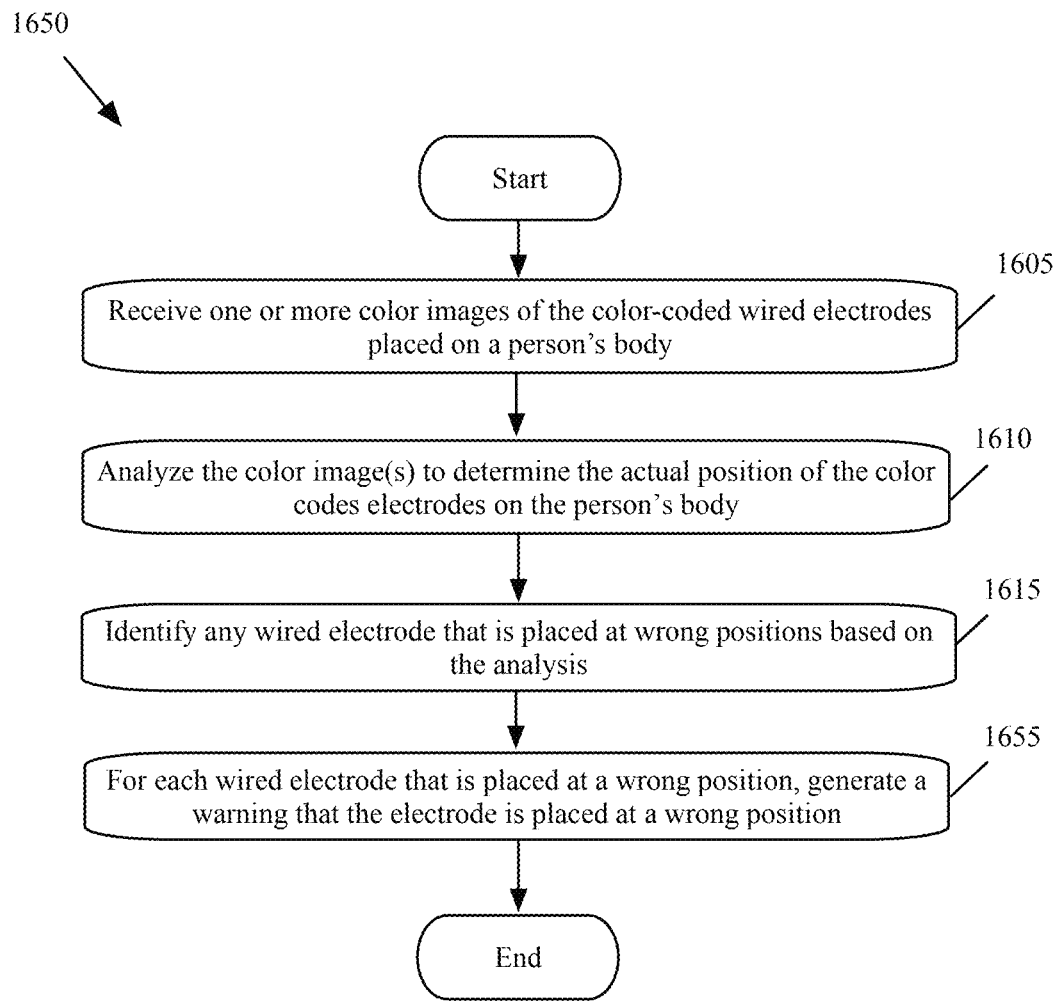
FIG. 16B is a flowchart illustrating an example process for identifying the wired electrodes that are placed at wrong positions on the body by analyzing color images and generating a warning for each electrodes that is placed at a wrong position, according to various aspects of the present disclosure.

FIG. 16B is a flowchart illustrating an example process 1650 for identifying the wired electrodes that are placed at wrong positions on the body by analyzing color images and generating a warning for each electrodes that is placed at a wrong position, according to various aspects of the present disclosure. The process 1650, in some of the present embodiments, may be performed by a processor of the ECG monitor or the processor of the connection box 305 of FIG. 3.

With reference to FIG. 16B, blocks 1605-1615 may be similar to the corresponding blocks of FIG. 16A. The process 1650, for each wired electrodes that is placed at a wrong position, may generate (at block 1655) a warning that the electrode is placed at a wrong position. The warning may be used by the health care personnel that are performing the ECG test. The warning may be in the form of an audio and/or a visual message. In addition to, or in lieu of the audio and/or the visual message, the wired electrodes may include a display or a light (e.g., one or more LEDs or a display, similar to the display 610 shown in FIG. 6 for a wireless electrode) that may blink when the process 1650 determines that the electrode is positioned at a wrong place to alert the medical health care personnel to correct the position of the wireless electrode. In some embodiments, the warning message may instruct the health care personnel to correct the position of the wired electrodes that are placed at wrong positions. The message may identify the visual indicator of the electrodes that are placed at wrong positions. The process 1550 may then end. It should be noted that some of the embodiments that instruct the health care personnel to correct the position of the wireless electrodes may not include the connection box 305 of FIG. 3. In these embodiments, the process 1650 may be performed by the processor of the ECG monitor.

In some embodiments, the electrodes that are positioned at wrong places on the body may be determined based on the distance between the electrodes. The electrodes in some of these embodiments may include internal clocks. The electrodes may have an internal clock and may synchronize their internal clocks. For example, in some embodiments, each electrode may include an accurate clock with no significant drift from each other over a period of a few hours or a few days. The clocks may be, for example, and without limitation, atomic clocks. The electrode clocks may be synchronized with each other.

Different embodiments may synchronize the electrode clocks differently. In some embodiments, the tray that recharges the electrode batteries (e.g., the tray 500) may be used to synchronize the electrode clocks. In some embodiments, the cardiac monitoring system may include a special tray for the purpose of synchronizing the clocks. The tray that is used to synchronize the electrode clocks (either the recharging tray or a special tray) may include a clock server and the shape of the tray may be made such that the distance between the clock server and each electrode's clock is the same with an accuracy that is better than a threshold (e.g., and without limitations, 1 millimeter (mm), 0.1 mm, etc.). The server may then send a signal (e.g., after an operator pushes a button) to all electrodes that are on the tray to synchronize their clocks.

In other embodiments, the electrode clocks may have access to a global clock and may synchronize with the global clock. Some embodiments may use clock synchronization methods that are well-known in the art to synchronize the electrode clocks. These methods may include, for example, and without limitations, using Berkeley algorithm, clock-sampling mutual network synchronization, Cristian's algorithm, Satellite navigation systems, Inter-range Instrumentation Group time codes, Network Time Protocol, Reference broadcast synchronization, Reference Broadcast Infrastructure Synchronization, Synchronous Ethernet, Wireless ad hoc networks, Huygens algorithm, H-tree clock distribution, etc.

Some embodiments may synchronize the electrodes that are being used in the same ECG test prior to the start of each test. Other embodiments may synchronize the electrodes that are being used in the same ECG tests only once until the electrodes are recharged.

Figure 17:
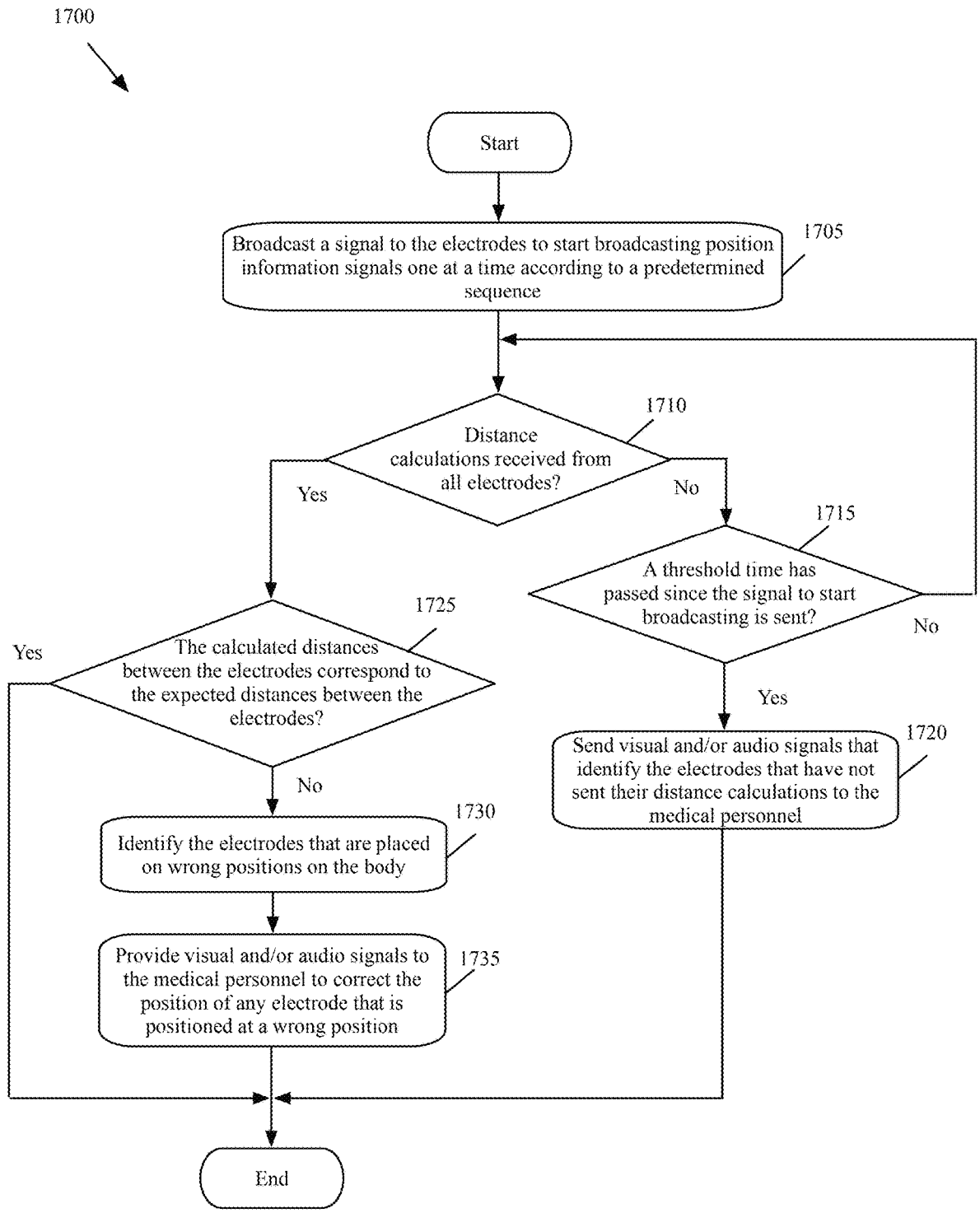
FIG. 17 is a flowchart illustrating an example process for identifying the wireless electrodes that are placed at wrong positions on the body based on the distance between the electrodes, according to various aspects of the present disclosure.

FIG. 17 is a flowchart illustrating an example process 1700 for identifying the wireless electrodes that are placed at wrong positions on the body based on the distance between the electrodes, according to various aspects of the present disclosure. The process 1700, in some of the present embodiments, may be performed by a processor of the wireless cardiac monitoring system 100 of FIG. 1 (e.g., by a processor of the preprocessing unit 135 or a processor of the ECG monitor 110 in the embodiments that the preprocessing unit does not have a processor).

Figure 18A:
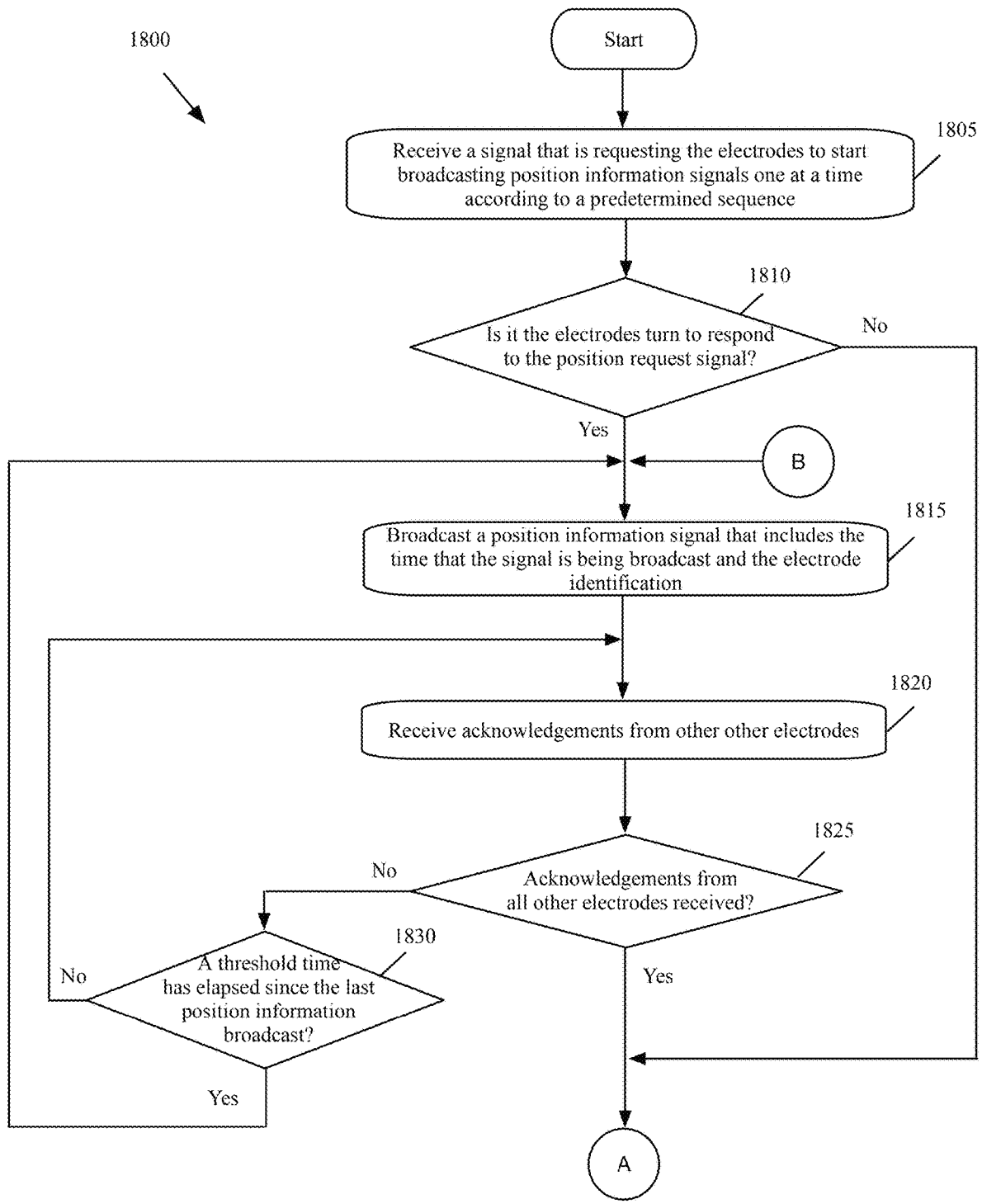
FIGS. 18A-18B illustrate a flowchart of an example process performed by each electrode for calculating the mutual distance between every pair of electrodes, according to various aspects of the present disclosure.
Figure 18B:
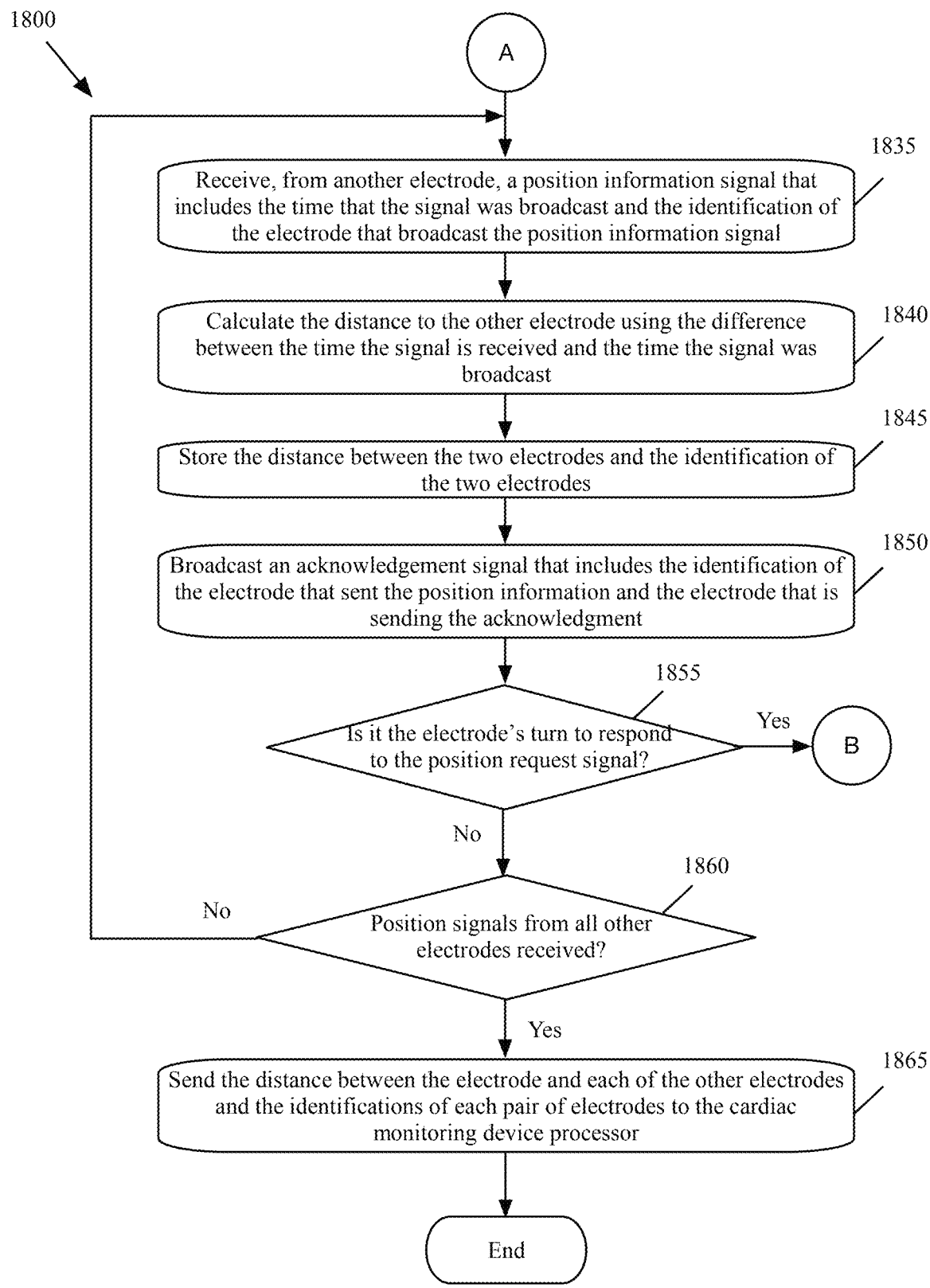

FIGS. 18A-18B illustrate a flowchart of an example process 1800 performed by each electrode for calculating the mutual distance between every pair of electrodes, according to various aspects of the present disclosure. The process 1800, in some of the present embodiments, may be performed by a processor of the electrodes (e.g., the processor 740 of the electrodes). The process 1700 may start after the clocks of the electrodes that are being used in an ECG test are synchronized by each other. Determining the electrodes that are positioned at wrong places on the body based on the distance between the electrodes are described with reference to processes 1700 and 1800.

The process 1700 may start after the electrodes are placed on the person's body. For example, in some embodiments, a medical personnel in attendance may push a button after the electrodes are placed on the body. In some embodiments, the button may be the same button that is used to start the ECG test. In other embodiments, the button may be different than the button that starts the ECG test. The processor of the cardiac monitoring system may receive the signal indicating that the electrodes are placed on the person's body and may start the process 1700.

With reference to FIG. 17, a signal may be broadcast (at block 1705) to the electrodes to start broadcasting position information signals one at a time according to a predetermined sequence. The electrodes may broadcast their position information signals in a sequence that is determined by their position codes, by their identifications, by a sequential number that is assigned to each electrode, etc. Each electrode may be configured to know how many other electrodes are being used for the ECG test. Each electrode may be configured to know its own position in the sequence.

With reference to FIG. 18A, an electrode may receive (at block 1805) a signal that is requesting the electrodes to start broadcasting position information signals one at a time according to a predetermined sequence. For example, the electrode may receive the signal that was broadcast by the process 1700 at block 1705. It should be noted that the steps 1805-1865 of the process 1800 may be performed by each electrode that is placed on the body.

A determination may be made (at block 1810) whether it is the electrode's turn to respond to the position request signal. As described above, each electrode may be configured to know its own position in the sequence. If the electrode is the first electrode in the sequence, the process 1800 may proceed to block 1815 to broadcast the electrode's position signal. Otherwise, the process 1800 may proceed to block 1835 (FIG. 18B) to receive the position information from other electrodes.

At block 1815, a position information signal that includes the time that the signal is being broadcast and the electrode identification may be broadcast. The position signal may include the time the electrode is transmitting the signal and the identification of the electrode. As described above, each electrode may include a clock and the clocks of all electrodes may be synchronized.

Acknowledgments from other electrodes may be received (at block 1820). A determination may be made (at block 1825) whether acknowledgments from all other electrodes are received. If not, a determination may be made (at block 1830) whether a threshold time has elapsed since the last position information broadcast. If not, the process 1800 may proceed to 1820, which was described above. Otherwise, if the threshold time has elapsed since the last position information broadcast and acknowledgments are not received from all other electrodes, the process 1800 may process to block 1815 to rebroadcast the position information in case some of the other electrodes were not able to receive the previous broadcast.

When a determination is made (at block 1825) that acknowledgements are received from all other electrodes, the process 1800 may proceed to block 1835 to receive position information from other electrodes and calculate the distance to the other electrodes. At block 1835, a position information signal that includes the time that the signal was broadcast and the identification of the electrode that broadcast the position information signal may be received from another electrode.

The distance to the other electrode may be calculated (at block 1840) using the difference between the time the signal is received and the time the signal was broadcast. Since the clocks of the electrode that sent the signal and the electrode that received the signal are synchronized, difference between the time the signal is received and the time the signal was broadcast is the time the electromagnetic signal took to reach the signal receiving electrode from the signal sending electrode. Dividing the time difference by the speed of electromagnetic waves (the speed of light) provide the distance between the two electrodes.

The distance between the two electrodes and the identification of the two electrodes may be stored (at block 1845). For example, the distance between the two electrodes and the identification of the two electrodes may be stored in the computer readable media 750 of FIG. 7. An acknowledgement signal that includes the identification of the electrode that sent the position information and the electrode that is sending the acknowledgment may be broadcast (at block 1850). As described above with reference to blocks 1815-1830, the electrode that sends the position signal expects to receive acknowledgment from all other electrodes and may repeat the signal broadcast if one or more electrodes do not send their acknowledgments.

A determination may be made (at block 1855) whether it is the electrode's turn to respond to the position request signal. As described above, each electrode may be configured to know its own position in the sequence. If the electrode is the next electrode in the sequence, the process 1800 may proceed to block 1815 to broadcast the electrode's position signal. Otherwise, a determination may be made (at block 1860) whether position signals from all other electrodes are received. If not, the process 1800 may proceed to block 1835 to receive position information from the next electrode in the sequence. Otherwise, the distance between the electrode and each of the other electrodes may be sent (at block 1865) to the cardiac monitoring device processor. Each distance may be identified by the identification of the two electrodes whose distance is measured. The process 1800 may then end.

Referring back to FIG. 17, a determination may be made (at block 1710) whether the distance calculations are received from all electrodes. If yes, the process 1700 may proceed to block 1725, which is described below. Otherwise, a determination may be made (at block 1715) whether a threshold time has elapsed since the signal to start broadcasting was sent. If not, the process 1700 may proceed to block 1710 to allow more time to all electrodes to send their position information. Otherwise, visual and/or audio signals that identify the electrodes that have not sent their distance calculations may be sent (at block 1720) to the medical personnel. the process 1700 may then end.

At block 1725, a determination may be made whether the calculated distances correspond to the expected distances between the electrodes. If yes, the process 1700 may end. Otherwise, the electrodes that are placed on wrong positions on the body may be identified. For example, any electrode whose distance with one or more other electrodes is not as expected may be identified as being placed at a wrong position. Visual and/or audio signals may be provided (at block 1735) to the medical personnel to correct the position of any electrode that is positioned at a wrong position. The process 1700 may then end.

The medical personnel may be alerted visually (e.g., by displaying a message on the display 125 of FIG. 1 or 3 and/or by blinking a light on the electrodes that need to be repositioned). In addition to, or in lieu of visually alerting the operator, the operator may be alerted by playing an audible message identifying the electrodes that have to be repositioned. Alternatively, the map signature of all possible misplacements may be stored and compared against the map signature obtained from the electrode placement to identify the errors.

For systems with a large number of electrodes, this exhaustive method may require a large number of searches and storage. However, if there are only a few electrode, or the number of incorrectly misplaced electrodes that may be detected is limited, the exhaustive search and the required storage may be significantly reduced. In some embodiments, the distance calculation may not be performed by the electrode processor at block 1840. In these embodiments, the electrode may send the position signal that the electrode receives from other electrodes to the processor of the cardiac monitoring system with the identification of both electrodes. In these embodiments, the distance calculations may be performed by process 1700.

In some other embodiments, when all electrodes are placed on the subject and the operator starts the ECG scan, the processor of the cardiac monitoring system may start a visual check by going through all electrodes one by one and issuing a command to flash a light on the electrode on and off a number of times while displaying on the screen the electrode number and position. The processor may also audibly announce the electrode number and position and may ask the operator to confirm the electrode is in the correct position. If an electrode is in the wrong position, it may be moved to the correct position by the operator.

Some of the above-described features and applications are implemented as software processes that are specified as a set of instructions recorded on a computer readable storage medium (also referred to as computer readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the term "software" is meant to include firmware residing in read-only memory or applications stored in magnetic storage, which can be read into memory for processing by a processor. Also, in some embodiments, multiple software inventions can be implemented as sub-parts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 19:
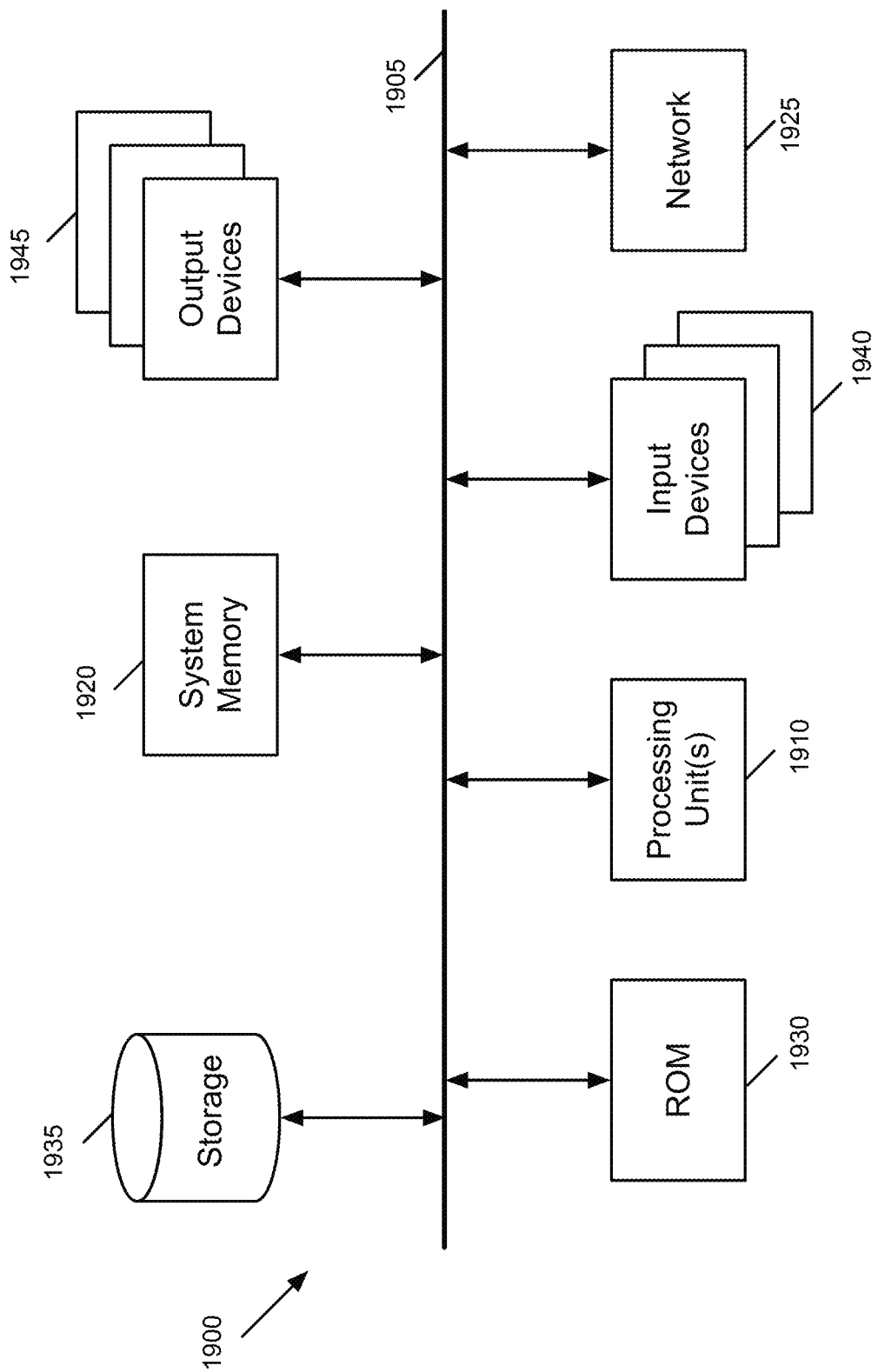
FIG. 19 is a functional block diagram of one example embodiment of an electronic system with which some embodiments of the invention are implemented.

FIG. 19 is a functional block diagram of one example embodiment of an electronic system 1900 with which some embodiments of the invention are implemented. The electronic system 1900 may be used to execute any of the control, virtualization, or operating system applications described above. The electronic system 1900 may be a computer (e.g., desktop computer, personal computer, tablet computer, server computer, mainframe, blade computer etc.), a controller, a microcontroller, or any other sort of electronic device. Such an electronic system includes various types of computer readable media and interfaces for various other types of computer readable media. Electronic system 1900 includes a bus 1905, processing unit(s) 1910, a system memory 1920, a read-only memory (ROM) 1930, a permanent storage device 1935, input devices 1940, and output devices 1945.

The bus 1905 collectively represents all system, peripheral, and chipset buses that communicatively connect the numerous internal devices of the electronic system 1900. For instance, the bus 1905 communicatively connects the processing unit(s) 1910 with the read-only memory 1930, the system memory 1920, and the permanent storage device 1935.

From these various memory units, the processing unit(s) 1910 retrieve instructions to execute and data to process in order to execute the processes of the invention. The processing unit(s) may be a single processor or a multi-core processor in different embodiments.

The read-only-memory 1930 stores static data and instructions that are needed by the processing unit(s) 1910 and other modules of the electronic system. The permanent storage device 1935, on the other hand, is a read-and-write memory device. This device is a non-volatile memory unit that stores instructions and data even when the electronic system 1900 is off. Some embodiments of the invention use a mass-storage device (such as a magnetic or optical disk and its corresponding disk drive) as the permanent storage device 1935.

Other embodiments use a removable storage device (such as a flash drive, etc.) as the permanent storage device. Like the permanent storage device 1935, the system memory 1920 is a read-and-write memory device. However, unlike storage device 1935, the system memory is a volatile read-and-write memory, such as random access memory. The system memory stores some of the instructions and data that the processor needs at runtime. In some embodiments, the invention's processes are stored in the system memory 1920, the permanent storage device 1935, and/or the read-only memory 1930. From these various memory units, the processing unit(s) 1910 retrieve instructions to execute and data to process in order to execute the processes of some embodiments.

The bus 1905 also connects to the input and output devices 1940 and 1945. The input devices enable the user to communicate information and select commands to the electronic system. The input devices 1940 include alphanumeric keyboards and pointing devices (also called "cursor control devices"). The output devices 1945 display images generated by the electronic system. The output devices include printers and display devices, such as cathode ray tubes (CRT) or liquid crystal displays (LCD). Some embodiments include devices, such as a touchscreen, that function as both input and output devices.

Finally, as shown in FIG. 19, the bus 1905 also couples electronic system 1900 to a network 1925 through a network adapter (not shown). In this manner, the computer can be a part of a network of computers (such as a local area network ("LAN"), a wide area network ("WAN"), an Intranet, or a network of networks, such as the Internet. Any or all components of electronic system 1900 may be used in conjunction with the invention.

Some embodiments include electronic components, such as microprocessors, storage, and memory, that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some embodiments are performed by one or more integrated circuits, such as application specific integrated circuits (ASICs) or field programmable gate arrays (FPGAs). In some embodiments, such integrated circuits execute instructions that are stored on the circuit itself.

As used in this specification, the terms "computer", "server", "processor", and "memory" all refer to electronic or other technological devices. These terms exclude people or groups of people. For the purposes of the specification, the terms display or displaying means displaying on an electronic device. As used in this specification, the terms "computer readable medium," "computer readable media," and "machine readable medium" are entirely restricted to tangible, physical objects that store information in a form that is readable by a computer. These terms exclude any wireless signals, wired download signals, and any other ephemeral or transitory signals.

In a first aspect, a cardiac monitoring system is provided. The cardiac monitoring system includes several wireless electrodes. Each wireless electrode is assigned a position code corresponding to a position from several positions on a body of a subject. The cardiac monitoring system includes a non-transitory computer readable medium storing several predetermined signal profiles. Each predetermined signal profile generated from signals received by several electrodes positioned at a position in the several positions on bodies of one or more persons. The cardiac monitoring system includes a processor configured to receive a signal from each wireless electrode after the start of monitoring cardiac activities of the subject. The signal from each wireless electrode includes signal received by the wireless electrode from the subject's heart and the position code assigned to the wireless electrode. The processor is configured to compare the profile of the signal received by each wireless electrode with the predetermined signal profile corresponding to the position code in the wireless electrode signal, and determine that the profile of the signal received by one or more wireless electrodes do not match the predetermined signal profile corresponding to the position code in the wireless electrode signal. The processor is configured to, for any wireless electrode whose signal profile did not match the predetermined signal profile corresponding to the position code in the wireless electrode signal: match the profile of the wireless electrode signal with another predetermine signal profile in the several predetermined signal profiles; and change the position code of the wireless electrode signal to the position code of the matched predetermined profile. The processor is configured to, after changing the position code of any wireless electrode whose signal profile did not match the predetermined signal profile corresponding to the position code: store the signal and the position code of the several wireless electrodes; and determine an electrocardiogram of the subject's heart using the stored signals and position codes of the several wireless electrodes.

In an embodiment of the first aspect, each wireless electrode includes an ADC that is configured to convert analog signals received from the subject's heart into digitized data; a wireless transceiver; and a processor configured to receive the digitized data from the ADC and transmit the digitized data to the processor of the cardiac monitoring system through the wireless transceiver.

In another embodiment of the first aspect, each wireless electrode further includes a non-transitory computer readable medium configured to store the position code of the wireless electrode. The processor of each wireless electrode is configured to retrieve the position code of the wireless electrode from the computer readable medium of the wireless electrode; and include the position code of the wireless electrode in the digitized data that is transmitted by the wireless transceiver of the wireless electrode.

In another embodiment of the first aspect, each wireless electrode further includes: a housing configured to hold the wireless transceiver, the ADC, and the processor; and a conductive patch configured to receive electrical signals from a person's heart when the patch is attached to the person's skin. The conductive patch includes a first connector configured to connect with a second connector on the housing of the wireless transceiver.

In another embodiment of the first aspect, the conductive patch and the first connector are disposable, and the housing, the wireless transceiver, the ADC, and the processor are reusable.

In another embodiment of the first aspect, each wireless electrode includes a housing, and a rechargeable battery placed inside the housing. The cardiac monitoring system further includes a tray that has several wireless chargers. Each wireless charger configured to wirelessly charge the battery of a wireless electrode that is brought in a vicinity of the wireless charger.

In another embodiment of the first aspect, each wireless charger includes a display, and the tray includes a processor configured to determine the charge level of a battery that is brought in a vicinity of a wireless charger of the tray; and display one of the charge level of the battery, a percentage of the battery charge left, or the number of ECG runs the battery may handle with the determined charge level on the display of the corresponding wireless charger.

In another embodiment of the first aspect, each wireless electrode includes a battery; a display; and a processor configured to determine a charge level of the battery of the wireless electrode; and display one of the charge level of the battery, a percentage of the battery charge left, or the number ECG runs the battery may handle with the determined charge level on the display of the wireless charger.

In a second aspect, a cardiac monitoring system is provided. The cardiac monitoring system includes several patches, Each electrode patch is assigned a position code corresponding to a position in several positions on a body of a subject. The cardiac monitoring system also includes several input ports; a first processor configured to process signals received at input ports of the cardiac monitoring system when each input port receives signals from an electrode patch that is placed at a specific position of the several positions on the body of the subject; and a connection box. The connection box includes a second processor; a switch; and a non-transitory computer readable medium storing several predetermined signal profiles. Each predetermined signal profile generated from signals received by several electrodes positioned at a position in the several positions on bodies of several persons. The second processor is configured to receive signals from each electrode patch after the start of monitoring cardiac activities of the subject. Each electrode patch signal includes a signal received by the electrode patch from the subject's heart and the position code assigned to the electrode patch. The second processor is configured to compare a profile of the signals received from each electrode patch with the predetermined signal profile corresponding to the position code in the electrode patch's signal; and determine that the profile of the signal received by one or more electrode patches do not match the predetermined signal profile corresponding to the position code in the electrode patch signal. The second processor is configured to, for any electrode patch whose signal profile did not match the predetermined signal profile corresponding to the position code in the electrode patch signal: match the profile of the electrode patch's signal with another predetermine signal profile in the several predetermined signal profiles; and change the position code of the electrode patch's signal to the position code of the matched predetermined profile. The second processor is configured to, after changing the position code of any electrode patch signal whose profile did not match the predetermined signal profile corresponding to the position code in the electrode patch signal, route each electrode patch signal, through the switch, to an input port of the cardiac monitoring system based on the position code in the electrode patch signal.

In an embodiment of the second aspect, the connection box further includes several inputs. Each input is connected to one of the several electrode patches by one or more wires. The connection box further includes several outputs. Each output is connected to one of the several input ports of the cardiac monitoring system by one or more wires. The second processor receives signals from the inputs of the connection box and routes the signals, through the switch, to the outputs of the connection box based on the position codes of the signals after changing the position code of any electrode patch signal whose profile did not match the predetermined signal profile corresponding to the position code in the electrode patch signal.

An embodiment of the second aspect further includes an ADC between each input of the connection box and the second processor, each ADC configured to convert analog signals received from an electrode patch into digital signals.

Another embodiment of the second aspect further includes an amplifier between each input of the connection box and the second processor. Each amplifier is configured to receive analog signals from a wired electrode; and amplify the analog signals received from the wired electrode.

An embodiment of the second aspect further includes a noise filter between each amplifier and the second processor. Each noise filter configured to filter noise from the amplified signals received from the corresponding amplifier.

In a third aspect, a cardiac monitoring system is provided. The cardiac monitoring system includes several color-coded electrodes. Each color-coded electrode has a color code. Each color-coded electrode is associated with a position code corresponding to a position in several positions on a body of a subject. The cardiac monitoring system includes a processor configured to: receive one or more color images of the electrodes positioned on a body of the subject; analyze the one or more color images to identify a profile of the body of the subject and a current position of each color-coded electrode on the body of the subject; compare the current position of each color-coded electrode with the position code associated with the color-coded electrode; determine that the current position of one or more color-coded electrodes do not match the position on the body of the subject that corresponds to the position code associated with the color-coded electrode; and for any color-coded electrode whose current position does not match the position on the body of the subject that corresponds to the position code associated with the color-coded electrode, generate a warning to change the position of the electrode.

In an embodiment of the third aspect, the warning includes sending a message to an electronic device associated with an operator of the cardiac monitoring system to change the position of the electrode.

In another embodiment of the third aspect, each color-coded electrode includes a display. The warning includes blinking the display of the color-coded electrode whose current position does not match the position on the body of the subject that corresponds to the position code associated with the color-coded electrode.

In a fourth aspect, a cardiac monitoring system is provided. The cardiac monitoring system includes several color-coded electrodes. Each color-coded electrode has a color code. Each color-coded electrode is associated with a position code corresponding to a position in several positions on a body of a subject. The cardiac monitoring system includes a processor configured to receive a color image of the electrodes positioned on a body of the subject; analyze the color image to identify a profile of the body of the subject and a current position of each color-coded electrode on the body of the subject; compare the current position of each color-coded electrode with the position code associated with the color-coded electrode; determine that the current position of one or more color-coded electrodes do not match the position on the body of the subject that corresponds to the position code associated with the color-coded electrode; receive a signal from each electrode in the several electrodes after a start of cardiac activity monitoring of the subject. Each electrode signal includes an electrical signal received by the electrode from the subject's heart and the position code associated with the electrode. The processor is configured to, for any electrode whose current position did not match the position on the body of the subject that corresponds to the position code associated with the color-coded electrode, change the position code of the electrode signal to the position code associated with the current position of the color-coded electrode. The processor configured to, after changing the position code of any electrode whose current position does not match the position on the body of the subject that corresponds to the position code associated with the color-coded electrode store the signal and the position code of the several wireless electrodes; and determine an electrocardiogram of the subject's heart using the stored signals and position codes of the several wireless electrodes.

While the invention has been described with reference to numerous specific details, one of ordinary skill in the art will recognize that the invention can be embodied in other specific forms without departing from the spirit of the invention. In addition, a number of the figures conceptually illustrate processes. The specific operations of these processes may not be performed in the exact order shown and described. The specific operations may not be performed in one continuous series of operations, and different specific operations may be performed in different embodiments. Furthermore, the process could be implemented using several sub-processes, or as part of a larger macro process.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. A cardiac monitoring system, comprising:
   a plurality of wireless electrodes, each wireless electrode in the plurality of wireless electrodes assigned a position code in a plurality of position codes, each position code in the plurality of position codes corresponding to a position in a plurality of positions on a body of a subject;
   a non-transitory computer readable medium storing a plurality of predetermined signal profiles, each predetermined signal profile generated from signals received by an electrode placed at a position in the plurality of positions on bodies of a plurality of persons, each predetermined signal profile associated with the position code corresponding to the body position where the electrode is placed; and
   a processor configured to:
      receive a signal from each wireless electrode in the plurality of wireless electrodes after a start of monitoring cardiac activities of the subject, the signal from each wireless electrode comprising a signal received by the wireless electrode from the subject's heart and the position code assigned to the wireless electrode;
      compare a profile of the signal received by each wireless electrode with the predetermined signal profile associated with the position code in the wireless electrode signal;
      determine that the profile of the signal received by from a set of one or more wireless electrodes do not match the predetermined signal profile corresponding to the position code in the wireless electrode signal;
      for each wireless electrode in the set of wireless electrodes:
         match the profile of the wireless electrode signal with another predetermine signal profile in the plurality of predetermined signal profiles; and
         change the position code of the wireless electrode signal to the position code of the matched predetermined profile;
      after changing the position code of the one or more wireless electrodes in the set of wireless electrodes:
         store the signal and the position code of the plurality of wireless electrodes; and
         determine an electrocardiogram of the subject's heart using the stored signals and position codes of the plurality of wireless electrodes.

2. The cardiac monitoring system of claim 1, wherein each wireless electrode comprises:
   an analog to digital converter (ADC) configured to convert analog signals received from the subject's heart into digitized data;
   a wireless transceiver; and
   a processor configured to receive the digitized data from the ADC and transmit the digitized data to the processor of the cardiac monitoring system through the wireless transceiver.

3. The cardiac monitoring system of claim 2, wherein each wireless electrode further comprises:
   a non-transitory computer readable medium configured to store the position code of the wireless electrode,
   wherein the processor of each wireless electrode is configured to retrieve the position code of the wireless electrode from the computer readable medium of the wireless electrode; and
   include the position code of the wireless electrode in the digitized data that is transmitted by the wireless transceiver of the wireless electrode.

4. The cardiac monitoring system of claim 2, wherein each wireless electrode further comprises:
   a housing configured to hold the wireless transceiver, the ADC, and the processor of the wireless electrode; and
   a conductive patch configured to receive electrical signals from a person's heart when the patch is attached to the person's skin;
   wherein the conductive patch comprises a first connector configured to connect with a second connector on the housing of the wireless transceiver.

5. The cardiac monitoring system of claim 4, wherein the conductive patch and the first connector of each wireless electrode are disposable, and wherein the housing, the wireless transceiver, the ADC, and the processor of each wireless electrode are reusable.

6. The cardiac monitoring system of claim 1, wherein each wireless electrode comprises a housing and a rechargeable battery placed inside the housing, wherein the cardiac monitoring system further comprises:
   a tray comprising a plurality of wireless chargers, each wireless charger configured to wirelessly charge the battery of a wireless electrode that is brought to a vicinity of the wireless charger.

7. The cardiac monitoring system of claim 6, wherein each wireless charger comprises a display, and wherein the tray comprises a processor configured to:
   determine a charge level of a battery that is brought to a vicinity of a wireless charger of the tray; and
   display one of the charge level of the battery, a percentage of the battery charge left, or a number of electrocardiogram (ECG) runs the battery may handle with the determined charge level on the display of the corresponding wireless charger.

8. The cardiac monitoring system of claim 1, wherein each wireless electrode comprises:
   a battery;
   a display; and
   a processor configured to:
      determine a charge level of the battery of the wireless electrode; and
      display one of the charge level of the battery, a percentage of the battery charge left, or a number of electrocardiogram (ECG) runs the battery may handle with the determined charge level on the display of the wireless charger electrode.

9. The cardiac monitoring system of claim 1, wherein each wireless electrode comprises:
   an analog to digital converter (ADC) configured to convert analog signals received from the subject's heart into digitized data samples;
   a non-transitory computer readable medium;
   a wireless transceiver; and
   a processor configured to:
      receive the digitized data samples from the ADC;
      store a plurality of digitized data samples in the non-transitory computer readable medium of the wireless electrode; and transmit the plurality of digitized data to the processor of the cardiac monitoring system through the wireless transceiver.

\* \* \* \* \*